(12) United States Patent
Choi et al.

(10) Patent No.: US 12,350,512 B2
(45) Date of Patent: Jul. 8, 2025

(54) MASK AND SKIN CARE DEVICE INCLUDING SAME

(71) Applicant: LG INNOTEK CO., LTD., Seoul (KR)

(72) Inventors: Yong Jae Choi, Seoul (KR); Gyu Lin Lee, Seoul (KR); Do Hee Keum, Seoul (KR); Beom Sun Hong, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 979 days.

(21) Appl. No.: 17/436,135

(22) PCT Filed: Mar. 5, 2020

(86) PCT No.: PCT/KR2020/003108
§ 371 (c)(1),
(2) Date: Sep. 3, 2021

(87) PCT Pub. No.: WO2020/184898
PCT Pub. Date: Sep. 17, 2020

(65) Prior Publication Data
US 2022/0143419 A1   May 12, 2022

(30) Foreign Application Priority Data

Mar. 11, 2019 (KR) .................. 10-2019-0027265
Mar. 11, 2019 (KR) .................. 10-2019-0027275

(51) Int. Cl.
*A61N 5/06*         (2006.01)
*A45D 44/00*        (2006.01)
(Continued)

(52) U.S. Cl.
CPC .......... *A61N 5/0616* (2013.01); *A61N 1/0484* (2013.01); *A61N 1/328* (2013.01);
(Continued)

(58) Field of Classification Search
CPC ........ A45D 44/00; A61H 23/02; A61H 23/00; A61H 23/0245; A61M 37/00;
(Continued)

(56) References Cited

U.S. PATENT DOCUMENTS 8,454,550 B2   6/2013   Koenig et al.
9,061,128 B2   6/2015   Hall et al.
(Continued)

FOREIGN PATENT DOCUMENTS

AU   2003273110         1/2005
CA       2999499 A1 *   9/2014   ............. A61F 7/007
(Continued)

OTHER PUBLICATIONS

International Search Report dated Jun. 17, 2020 issued in Application No. PCT/KR2020/003108.
(Continued)

*Primary Examiner* — Jonathan T Kuo
*Assistant Examiner* — Vynn V Huh
(74) *Attorney, Agent, or Firm* — KED & ASSOCIATES, LLP

(57) ABSTRACT

A mask according to an embodiment comprises: a first substrate; a first wiring arranged on the first substrate; a plurality of piezoelectric elements arranged on the first wiring; a second wiring arranged on the piezoelectric elements; a second substrate arranged on the second wiring; a third wiring arranged on the first substrate and electrically insulated from the first wiring; and a plurality of light-emitting elements arranged between the first and second substrates and arranged on the third wiring, wherein the plurality of light-emitting elements are arranged in areas overlapping, in a vertical direction, areas between the piezoelectric elements.

14 Claims, 22 Drawing Sheets

(51) Int. Cl.
*A61H 23/02* (2006.01)
*A61M 37/00* (2006.01)
*A61N 1/04* (2006.01)
*A61N 1/32* (2006.01)
*A61N 7/00* (2006.01)

(52) U.S. Cl.
CPC ............... *A61N 2005/0626* (2013.01); *A61N 2005/0632* (2013.01); *A61N 2005/0647* (2013.01); *A61N 2005/0659* (2013.01); *A61N 2005/0662* (2013.01)

(58) Field of Classification Search
CPC ............... A61N 1/0484; A61N 1/328; A61N 5/06–2005/073; A61N 2007/0034
USPC ....................................... 607/88–94; 604/501
See application file for complete search history.

(56) References Cited

U.S. PATENT DOCUMENTS

| | | |
|---|---|---|
| 10,799,697 B2 | 10/2020 | Kim et al. |
| 2001/0029347 A1 | 10/2001 | Kasano |
| 2012/0029410 A1 | 2/2012 | Koenig et al. |
| 2015/0100002 A1 | 4/2015 | Choi |
| 2017/0239454 A1* | 8/2017 | Heath ................. A61M 35/003 |
| 2018/0352937 A1 | 12/2018 | Vandier et al. |
| 2019/0038912 A1* | 2/2019 | Song .................... A45D 44/002 |
| 2019/0105520 A1* | 4/2019 | Sverdlik ............ H10N 30/8554 |
| 2020/0121941 A1 | 4/2020 | Kwon et al. |
| 2020/0398074 A1 | 12/2020 | Lee |

FOREIGN PATENT DOCUMENTS

| | | | | |
|---|---|---|---|---|
| CN | 201510644 | 6/2010 | | |
| CN | 102316836 | 1/2012 | | |
| CN | 102772293 | 11/2012 | | |
| CN | 103566466 | 2/2014 | | |
| CN | 107041996 | 8/2017 | | |
| CN | 108348153 | 7/2018 | | |
| CN | 109069853 | 12/2018 | | |
| CN | 109395254 A * | 3/2019 | ............ | A61H 23/02 |
| KR | 20-0332096 | 11/2003 | | |
| KR | 20-0396456 | 9/2005 | | |
| KR | 10-2007-0053408 | 5/2007 | | |
| KR | 10-1214552 | 12/2012 | | |
| KR | 10-1384008 | 4/2014 | | |
| KR | 10-2015-0120114 | 10/2015 | | |
| KR | 10-2015-0124239 | 11/2015 | | |
| KR | 10-2015-0135335 | 12/2015 | | |
| KR | 10-1687583 | 12/2016 | | |
| KR | 10-2018-0038199 | 4/2018 | | |
| WO | WO-2013036558 A1 * | 3/2013 | ........... | A61F 9/0079 |
| WO | WO 2018/097428 | 5/2018 | | |
| WO | WO-2018097428 A2 * | 5/2018 | .............. | A61B 5/01 |
| WO | WO 2018/196310 | 11/2018 | | |
| WO | WO-2018196310 A1 * | 11/2018 | | |

OTHER PUBLICATIONS

Chinese Office Action dated Aug. 31, 2023 issued in Application No. 202080028864.8.

Chinese Office Action dated Dec. 26, 2022 issued in Application No. 202080028864.8.

* cited by examiner

[FIG. 1]
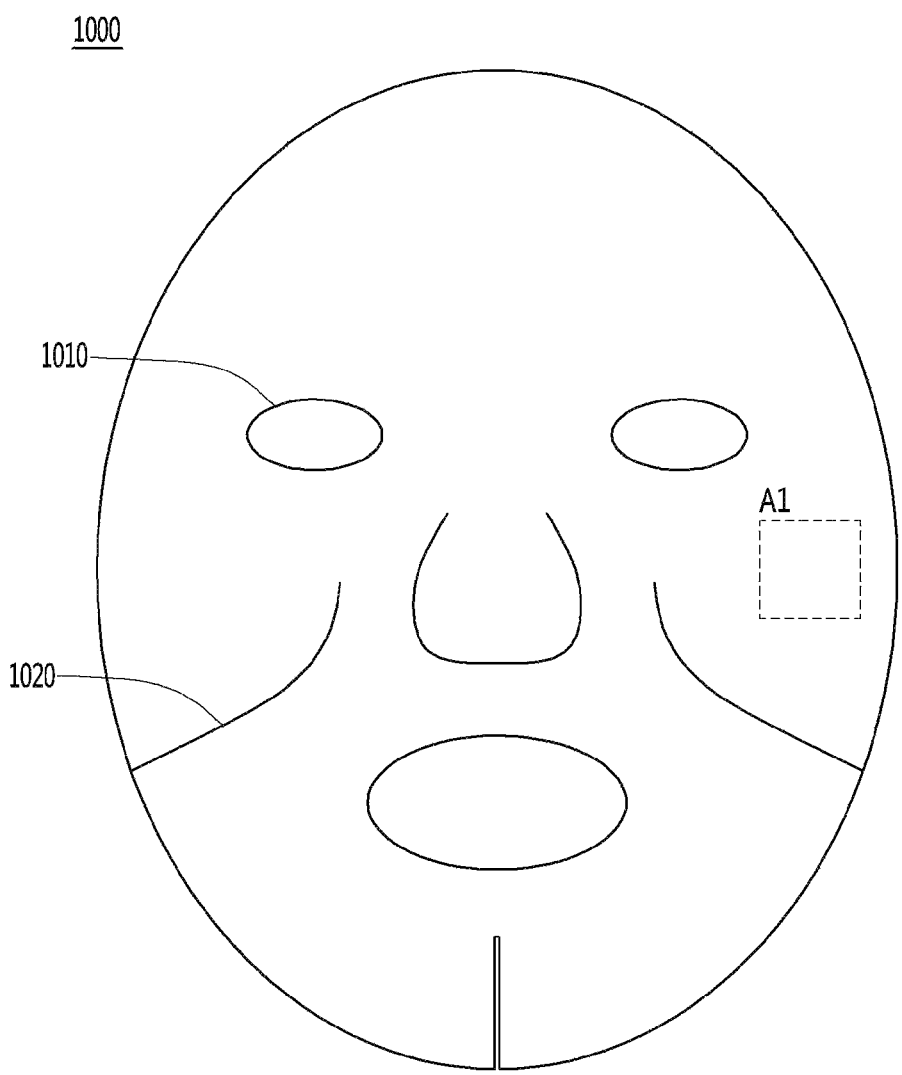

[FIG. 2]
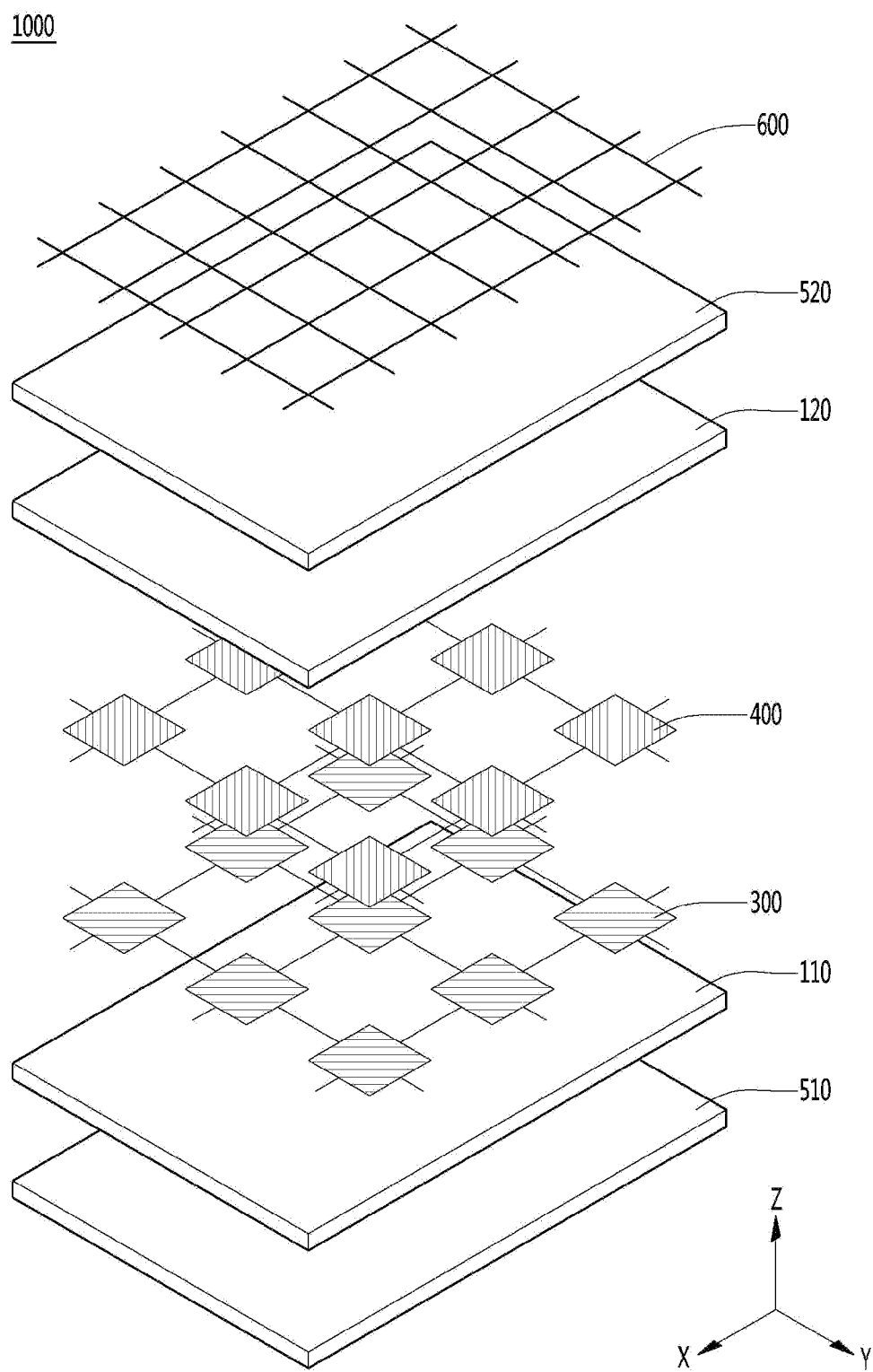

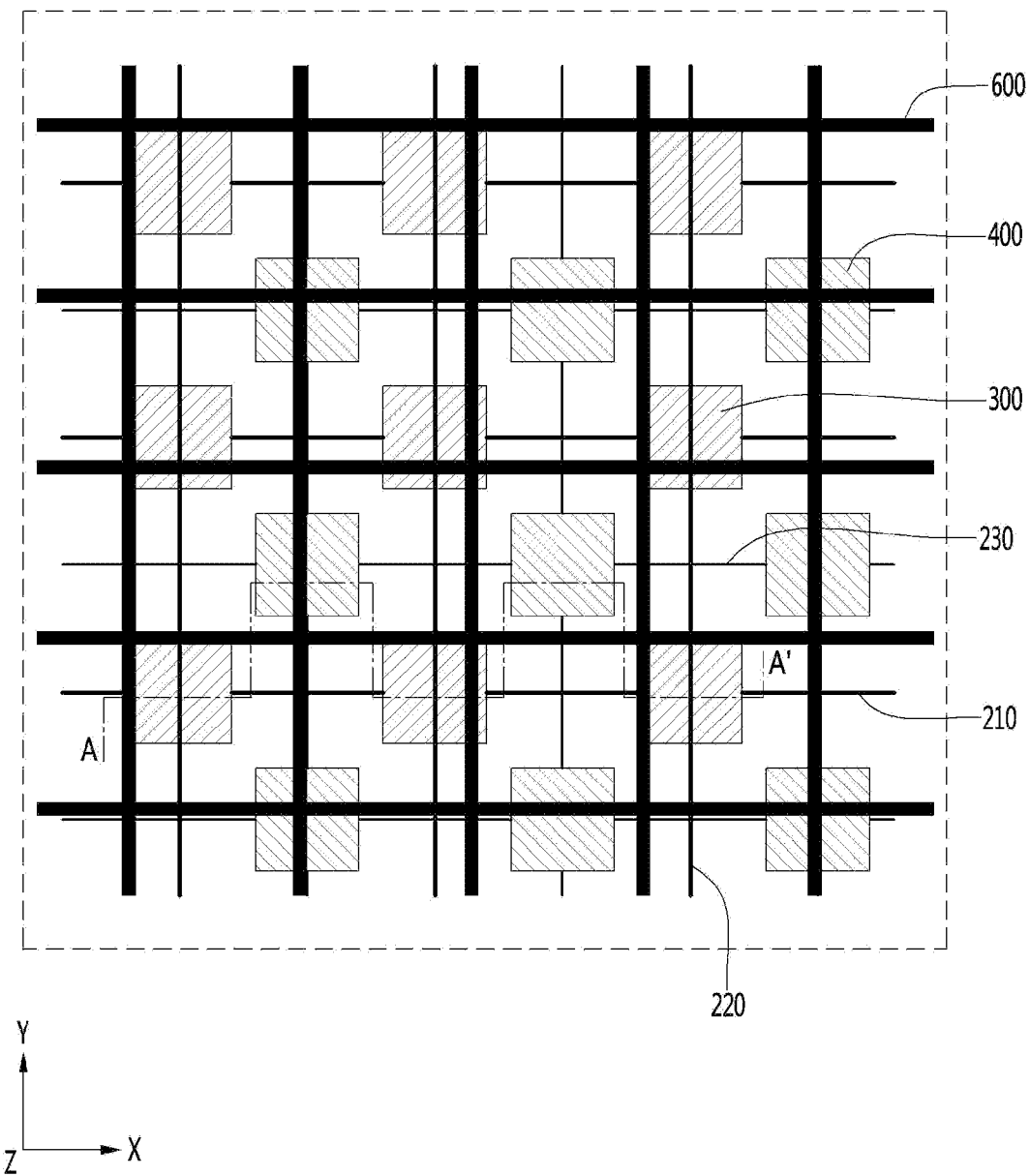

[FIG. 4]
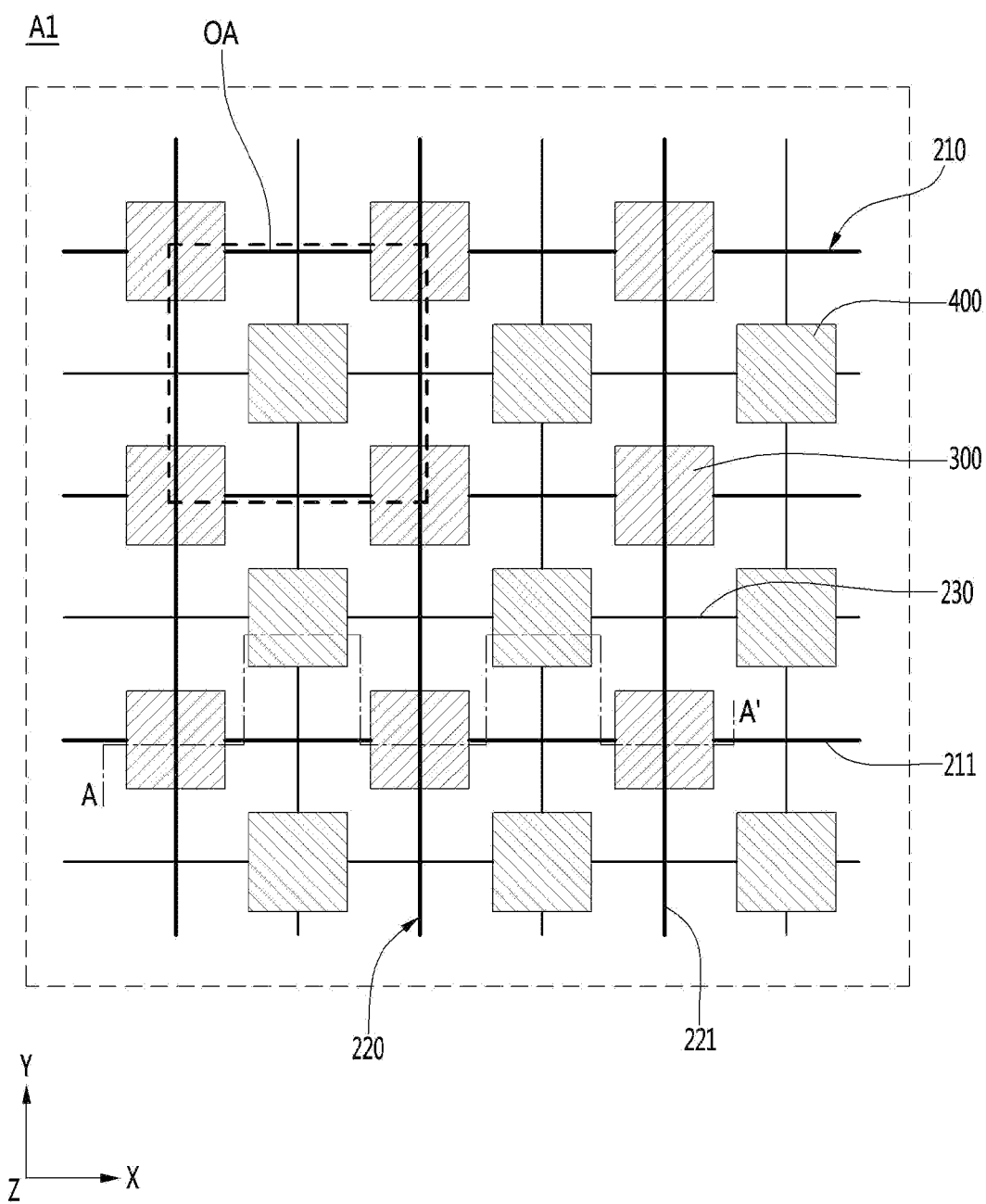

[FIG. 5]
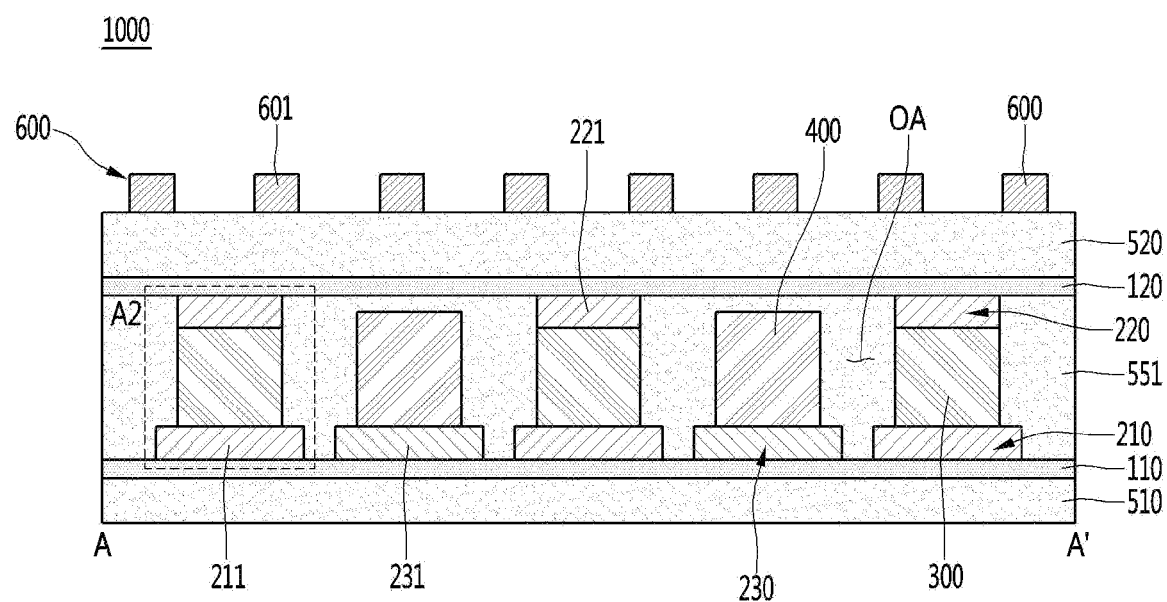

[FIG. 6]
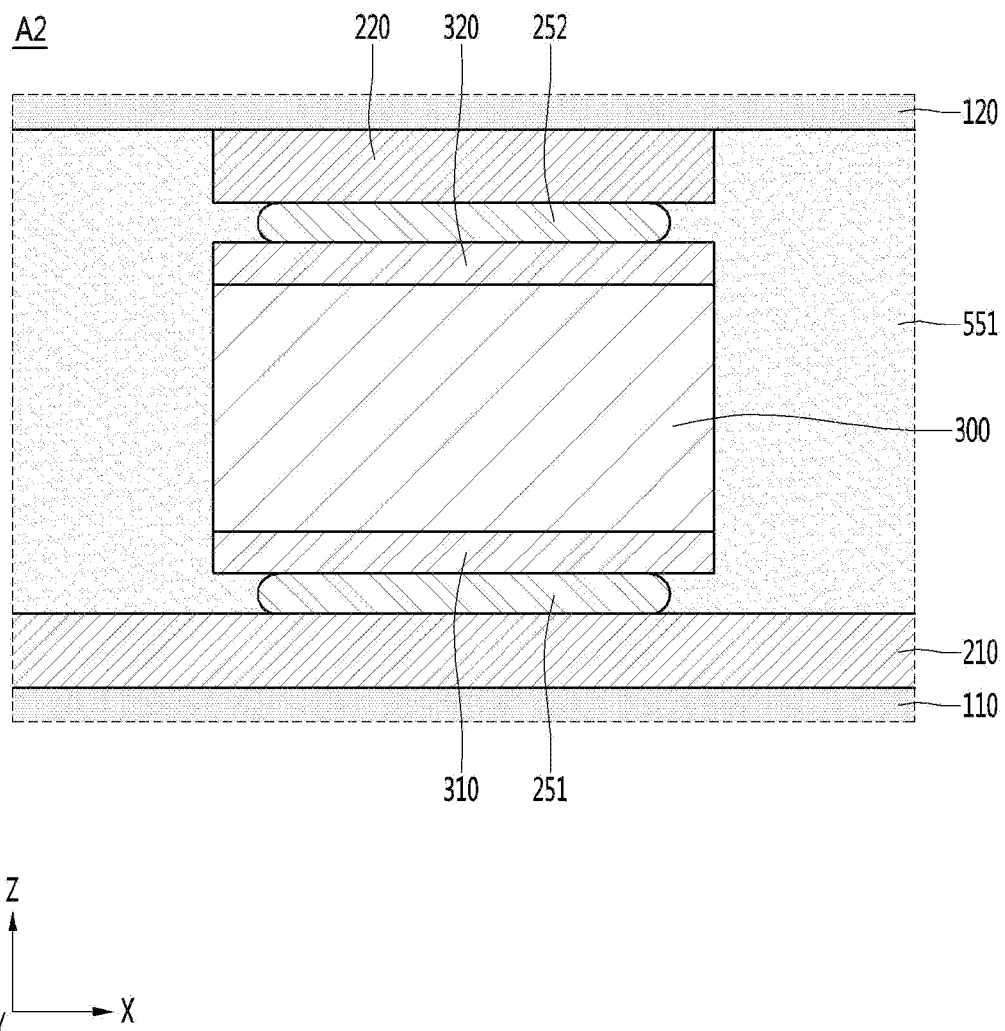

[FIG. 7]
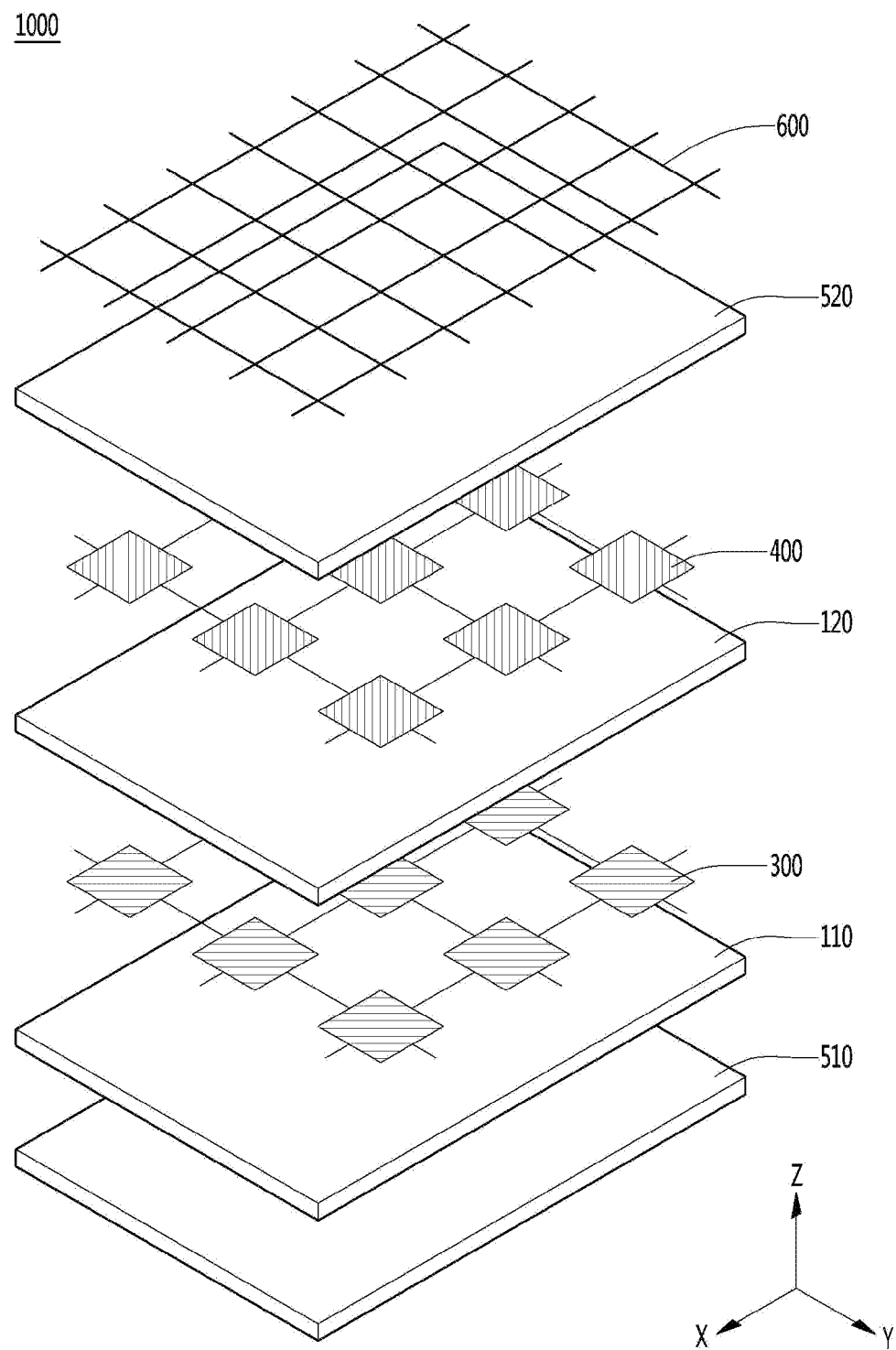

[FIG. 8]
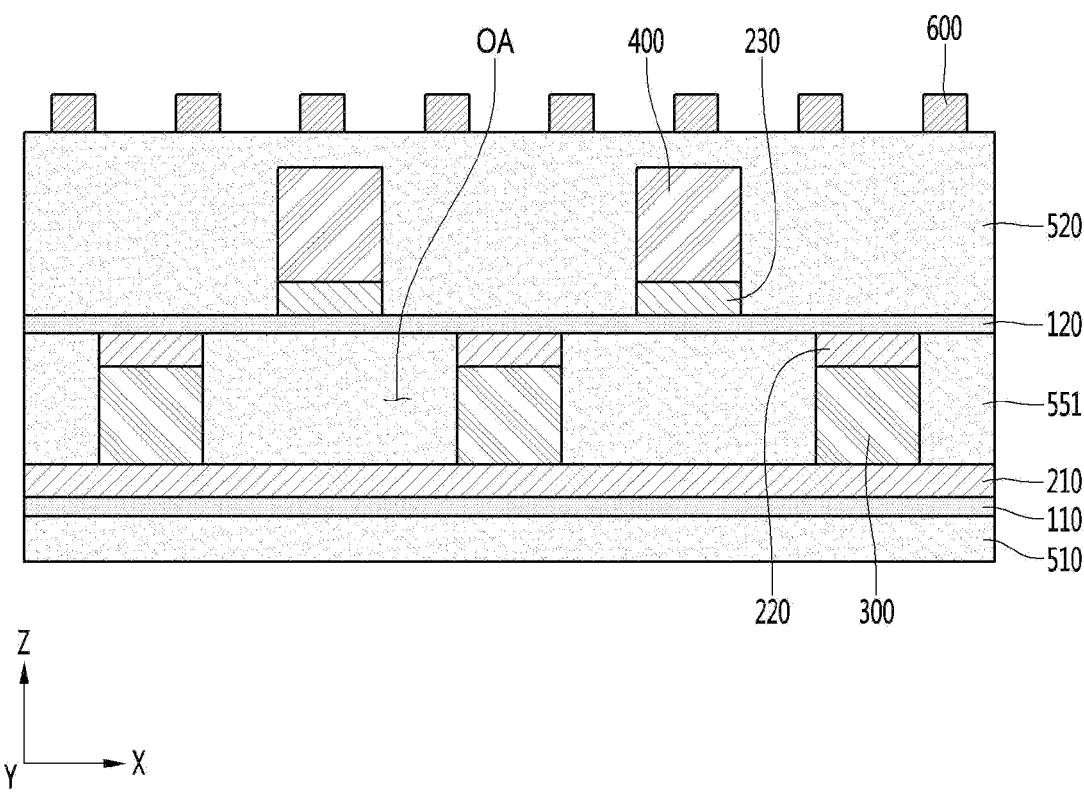

[FIG. 9]
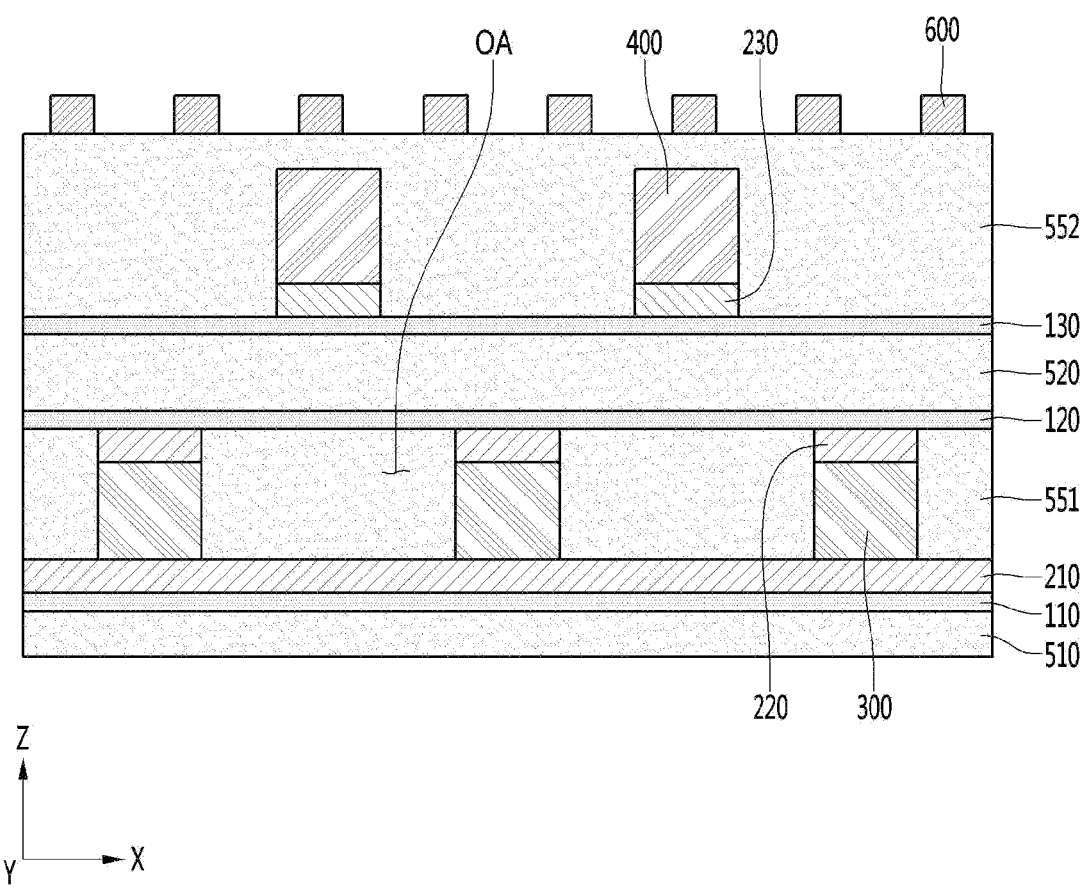

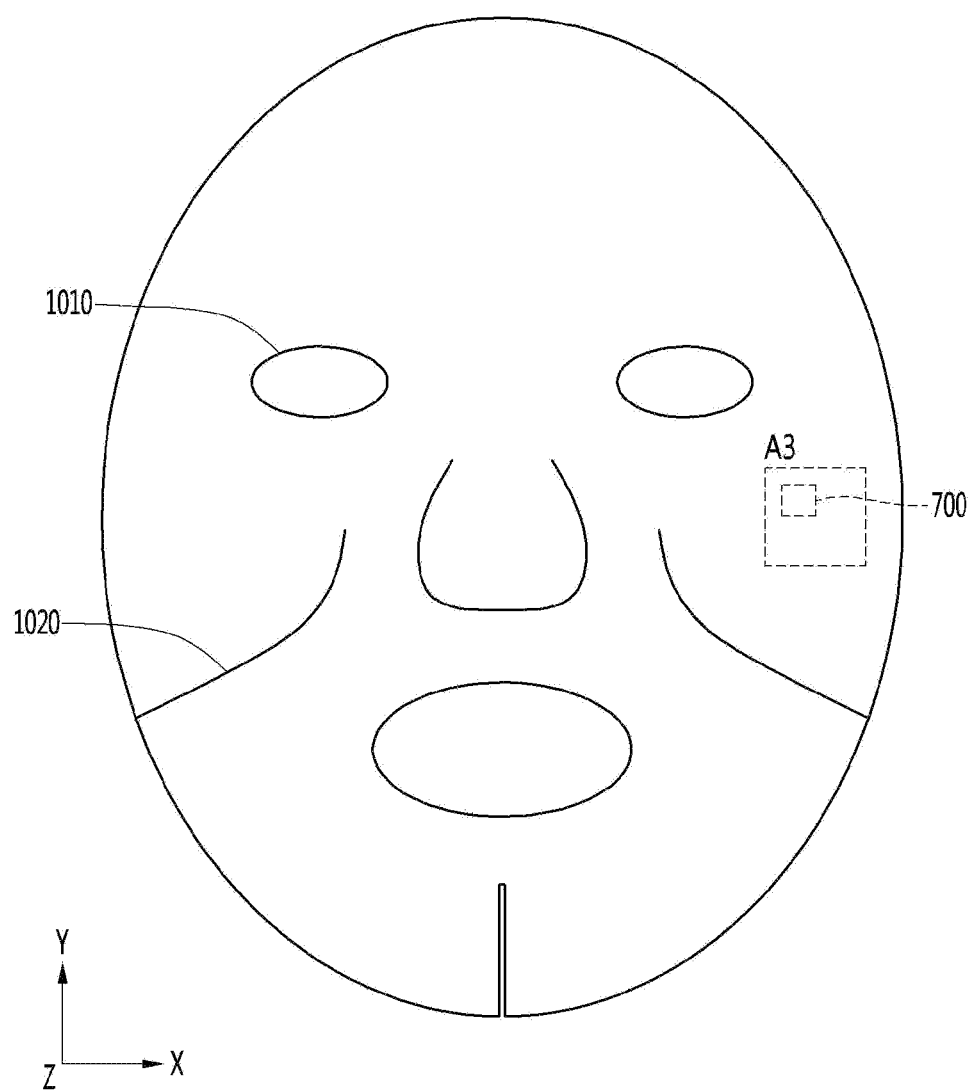

[FIG. 11]
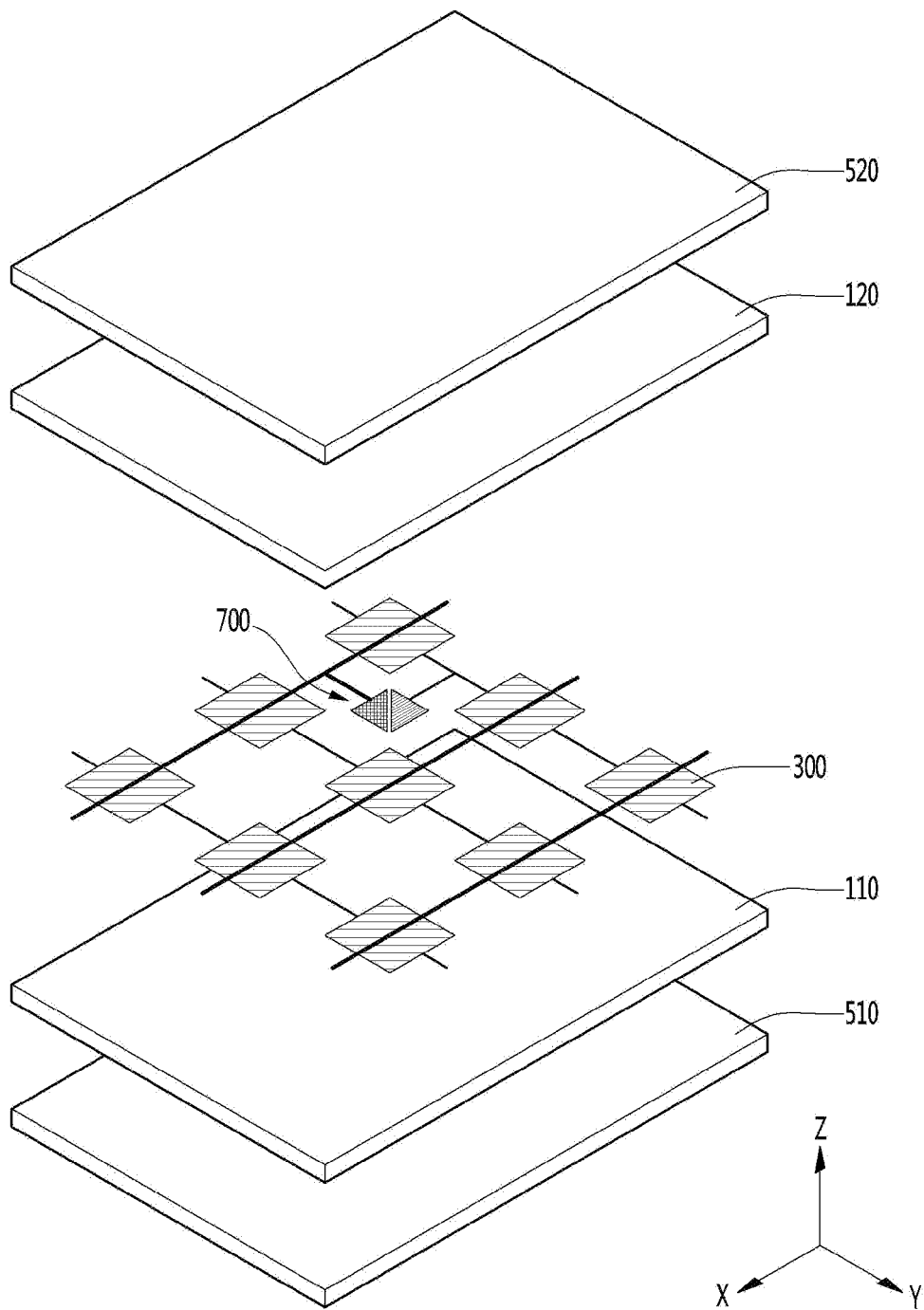

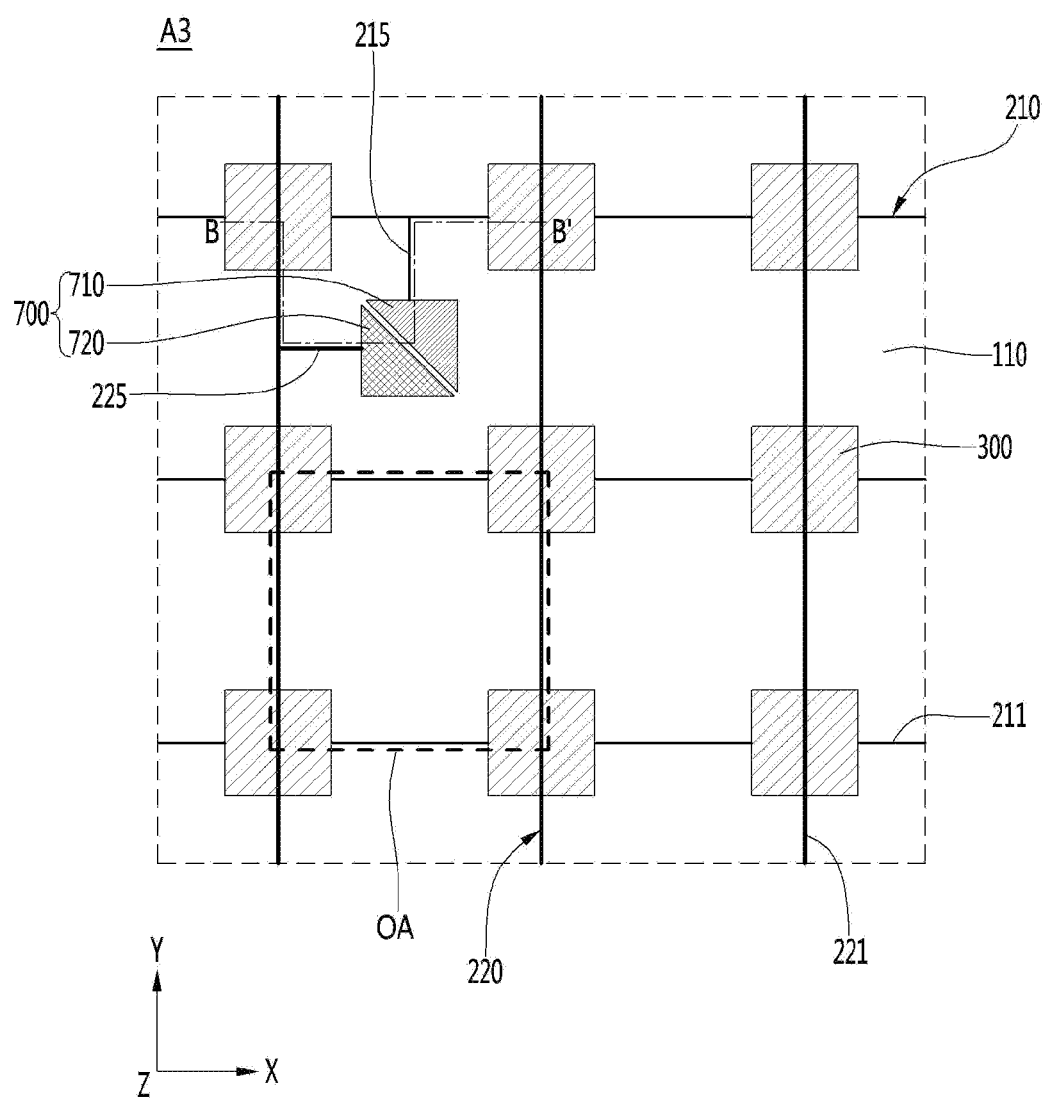
[FIG. 12]

【FIG. 13】
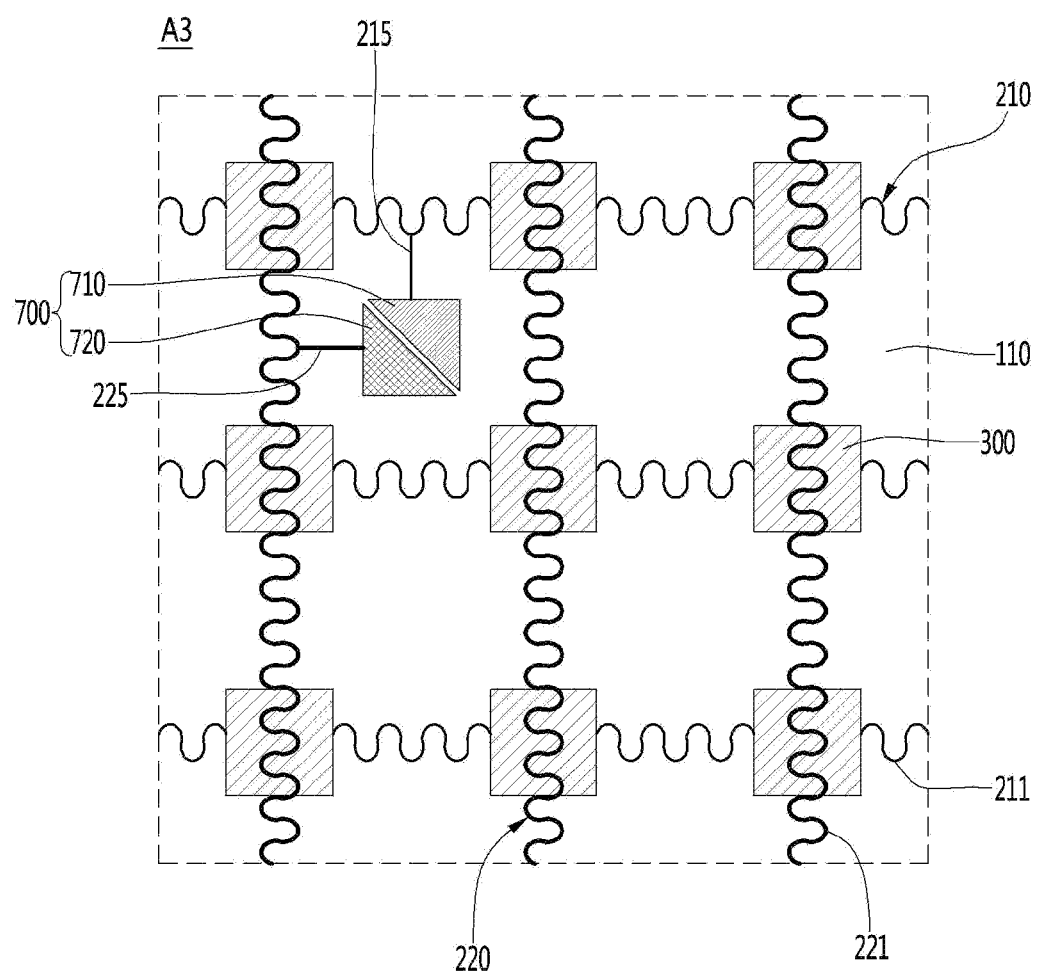

[FIG. 14]
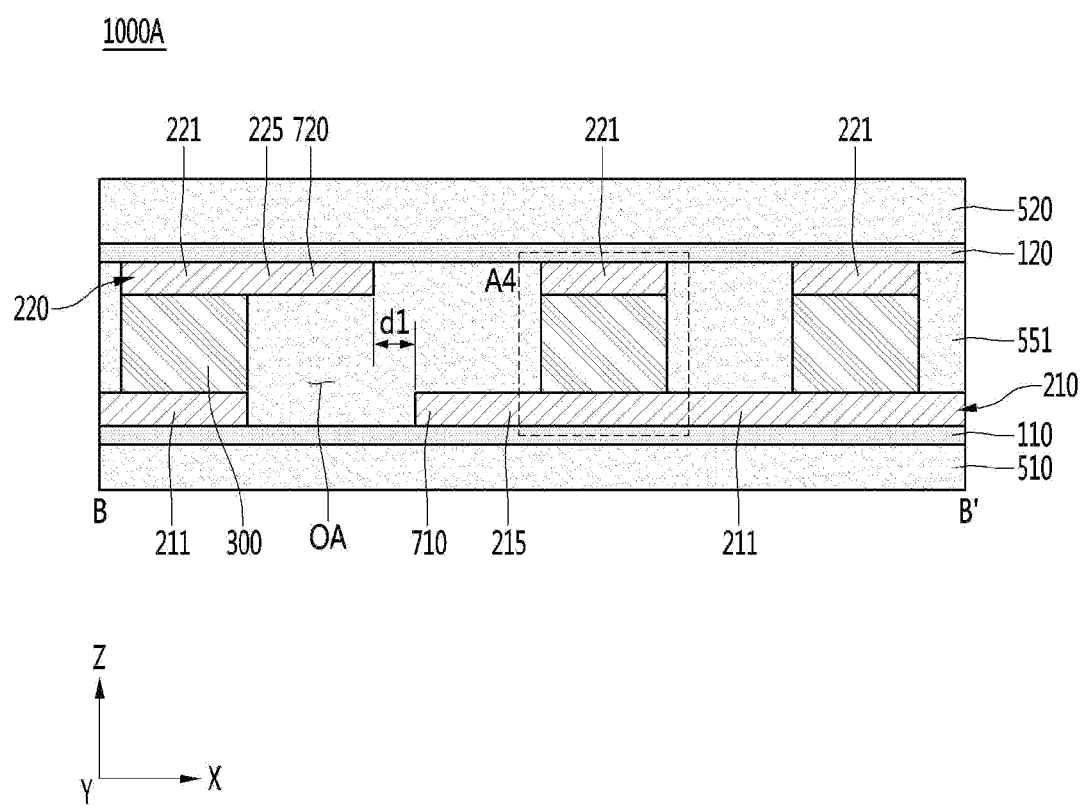

[FIG. 15]
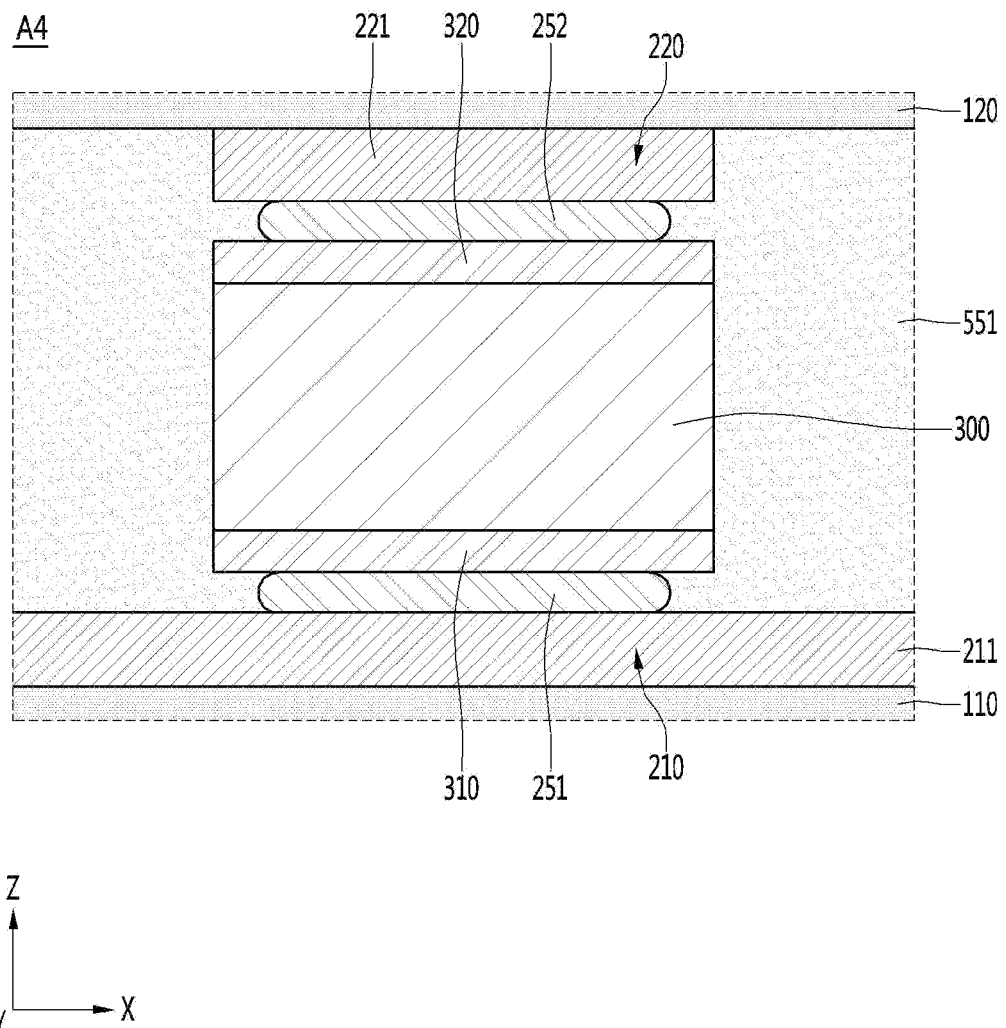

[FIG. 16]
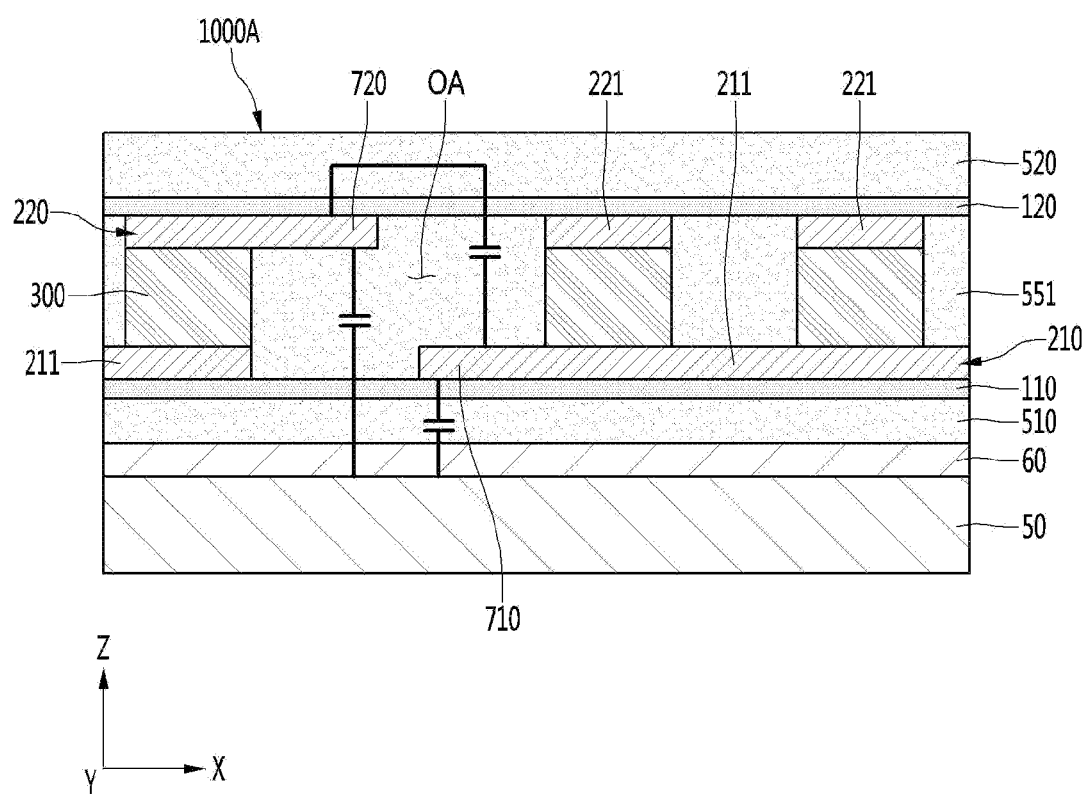

[FIG. 17]
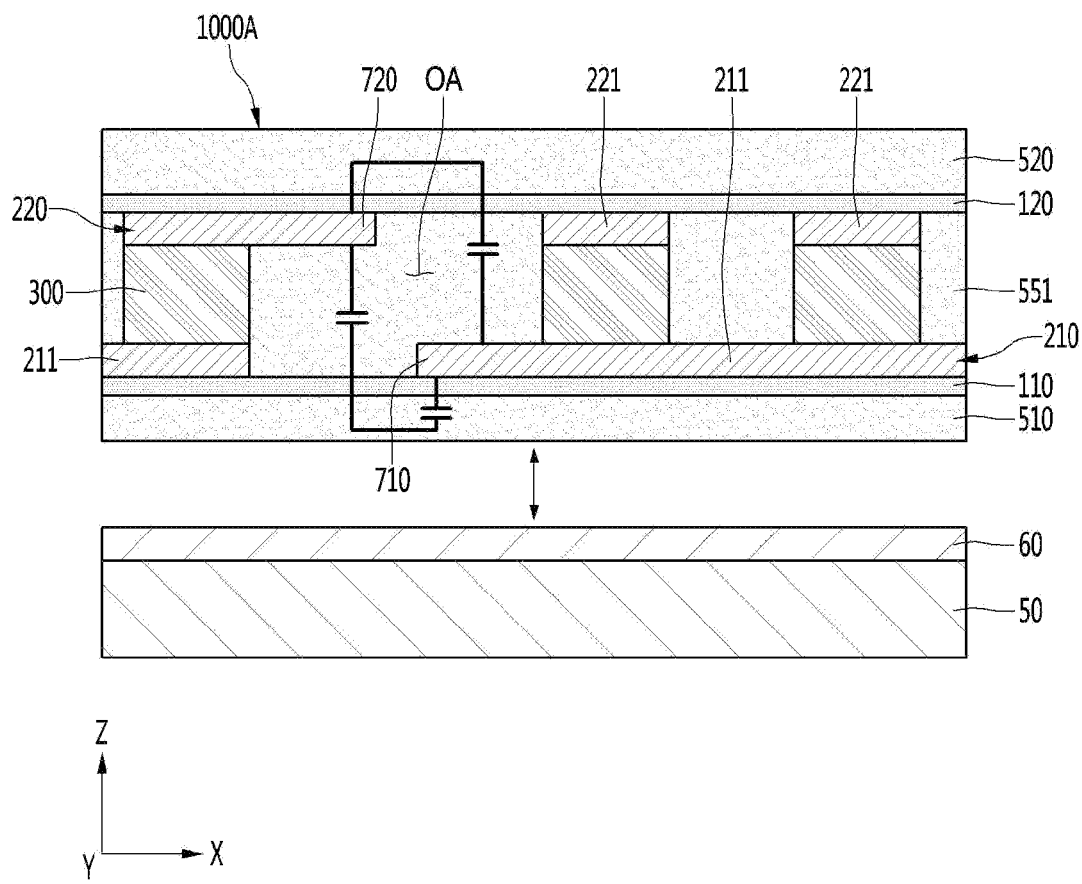

【FIG. 18】
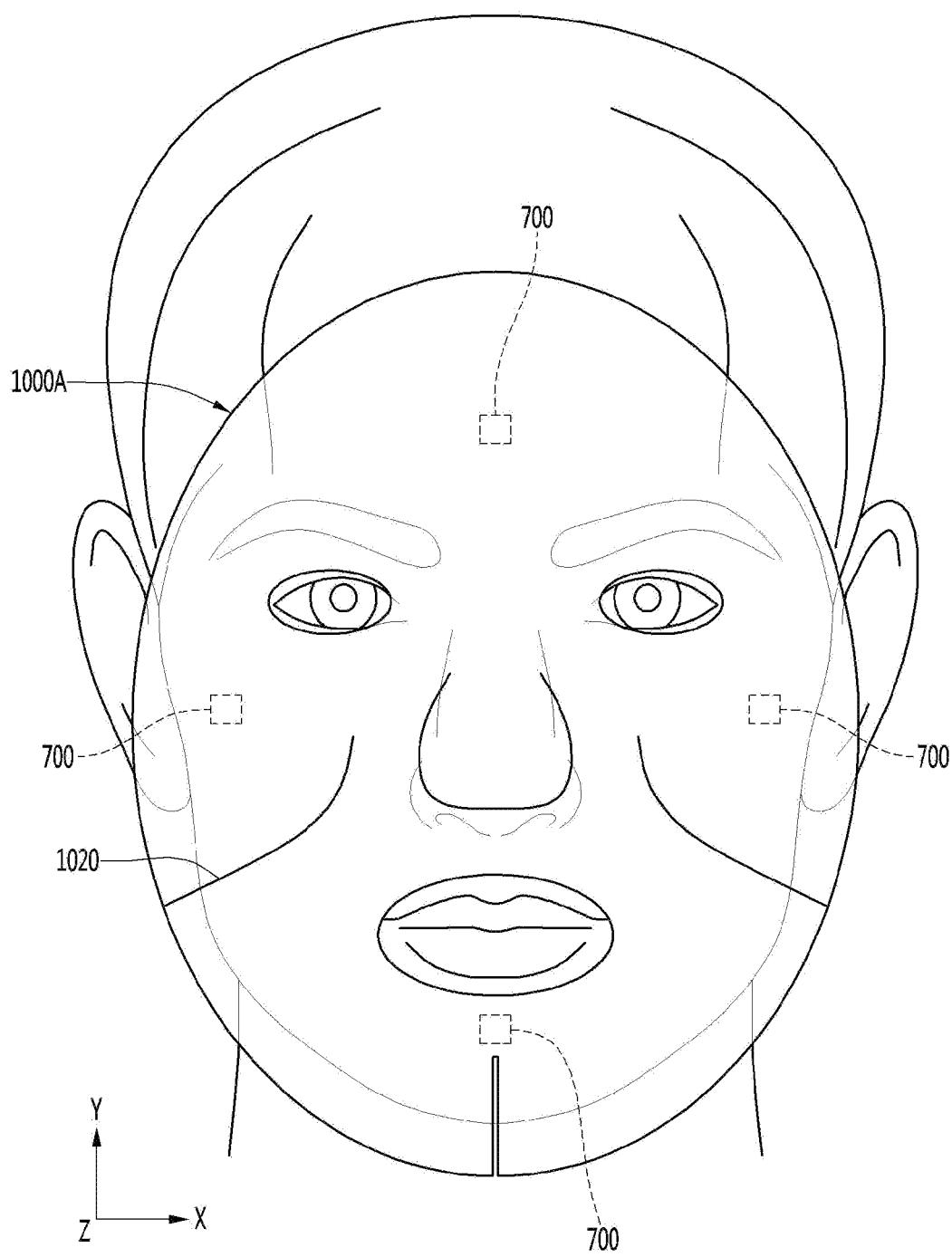

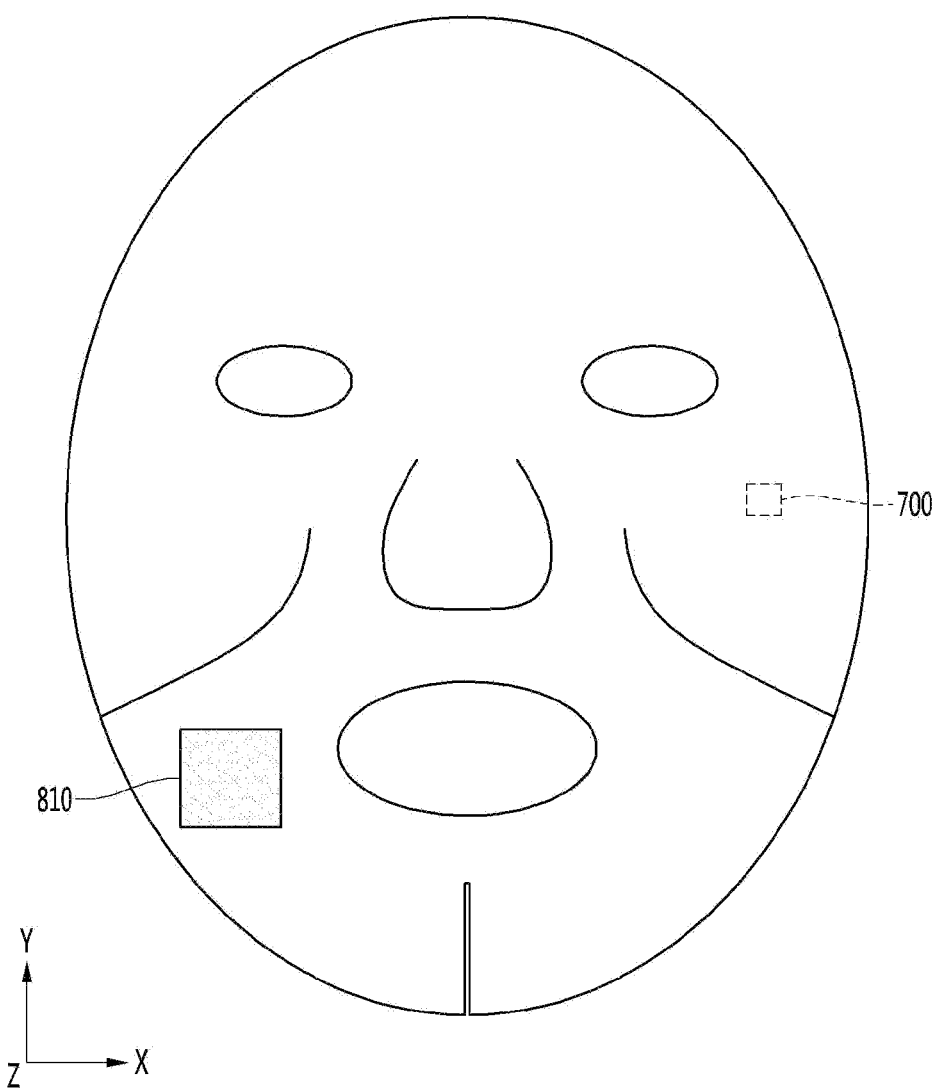
[FIG. 19]

[FIG. 20]
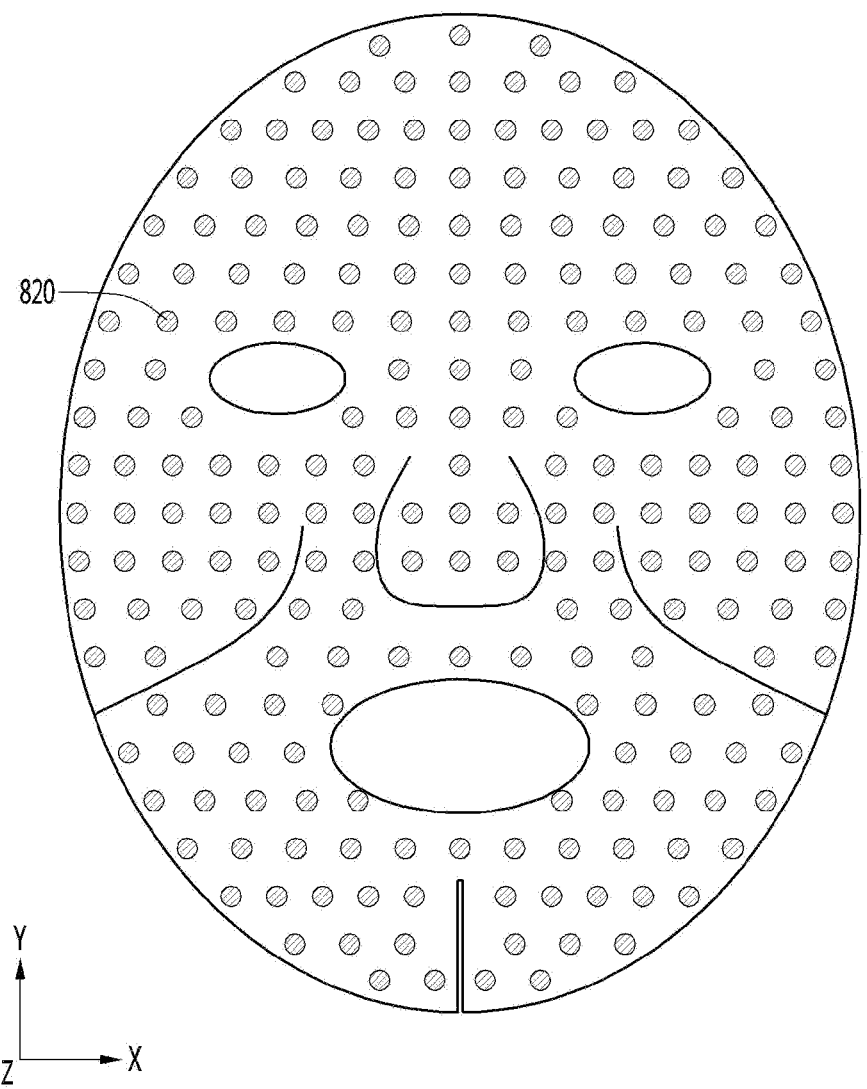

[FIG. 21]
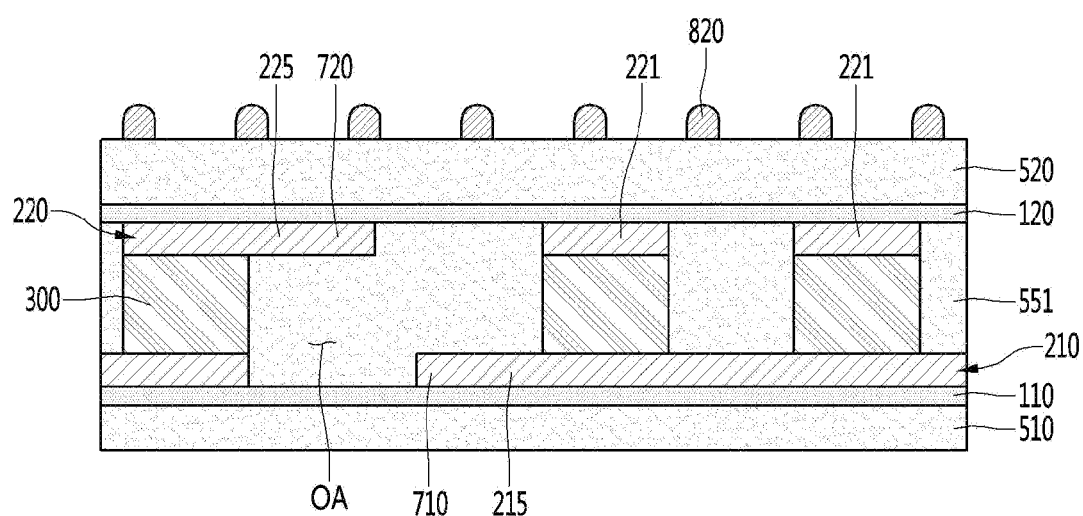

[FIG. 22]
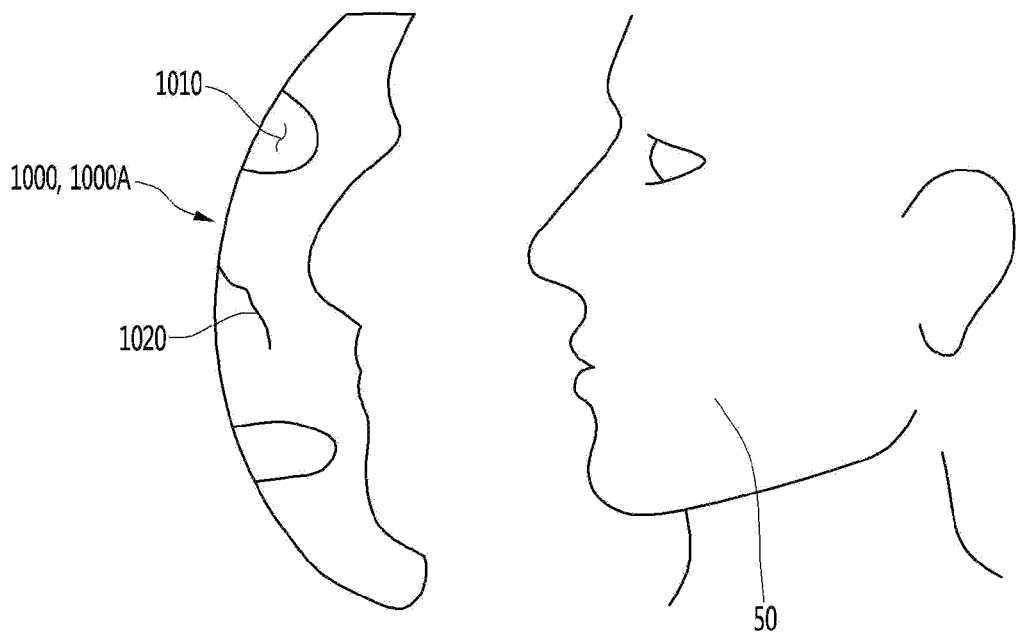
[FIG. 23]
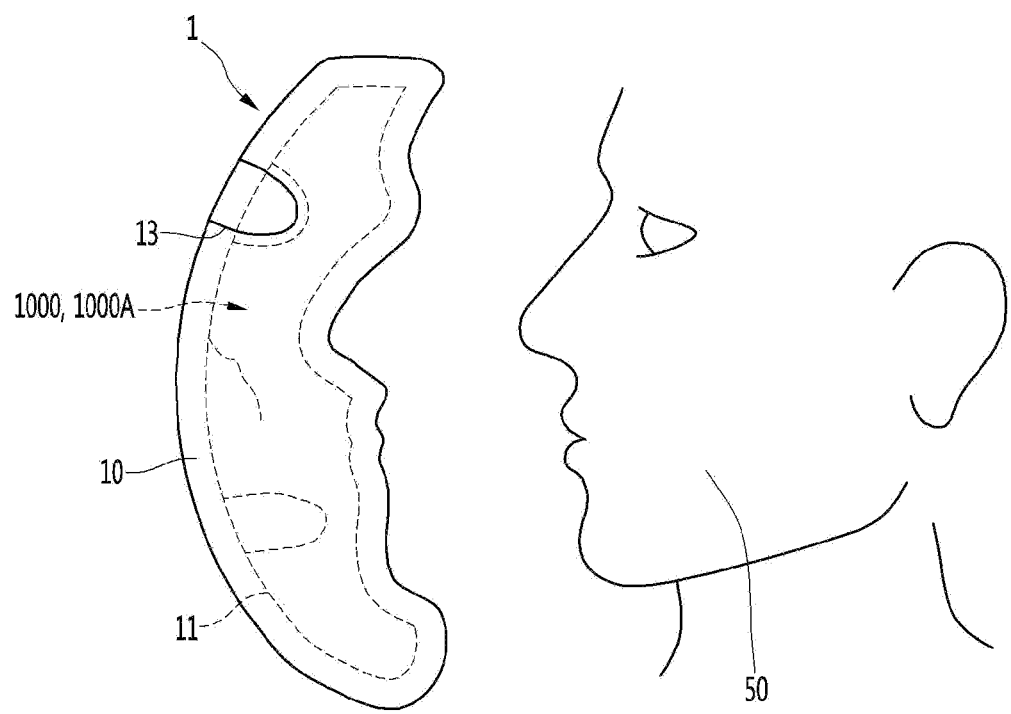

MASK AND SKIN CARE DEVICE INCLUDING SAME

CROSS-REFERENCE TO RELATED PATENT APPLICATIONS

This application is a U.S. National Stage Application under 35 U.S.C. § 371 of PCT Application No. PCT/KR2020/003108, filed Mar. 5, 2020, which claims priority to Korean Patent Application Nos. 10-2019-0027265 and 10-2019-0027275 both filed Mar. 11, 2019, whose entire disclosures are hereby incorporated by reference.

TECHNICAL FIELD

An embodiment relates to a mask and a skin care device.

BACKGROUND ART

Human skin may be damaged or contaminated depending on external factors such as environmental pollution, ultraviolet rays, stress, and the like, and wrinkles may occur due to internal factors such as aging, hormonal changes, and the like. Recently, as interest in the skin has increased, various devices for skin treatment, beauty, and anti-aging have been developed. In detail, a device has been developed, which is capable of applying thermal energy to the skin, for example, a device capable of improving skin elasticity by applying infrared energy. In addition, a device using sound waves or light rays has been developed in order to effectively inject cosmetics or drugs into the skin. For example, a device has been developed, which is capable of forming a path through which cosmetics or drugs are injected into the skin using sonophoresis and laserporation. In addition, a device has been developed, which is capable of effectively injecting cosmetics or drugs into the skin using electric propulsion force. For example, a device has been developed, which is capable of effectively injecting ionic substances contained in cosmetics or drugs into the skin using electric propulsion force such as iontophoresis, electroporation, and electroosmosis. That is, various devices have been developed, which is capable of caring or treating a user's skin by providing light energy, microcurrent, vibration, or the like to the skin.

In general, the above-described devices may be provided in a form of a patch detachable to the skin, and the devices are attached to a specific skin region to care or treat the skin of the attached region. In addition, the above-described devices may be provided in a form of a stick including a contact portion in contact with the skin, and the devices move and operate in a skin area requiring care or treatment while a user holds the device. At this time, the devices have a problem that it is difficult to effectively adhere to curved skin surfaces such as both cheeks, nose, and the like. In addition, since a size of the contact portion is limited, there is a problem that it is difficult to simultaneously care or treat the entire area of the skin, and there is a problem that it is difficult to evenly care for the entire area. In addition, when the user uses a function such as light energy, microcurrent, vibration, and the like, there is an inconvenience that the device should be changed according to the function.

In addition, the devices have a problem that it is difficult to effectively adhere to curved skin surfaces such as both cheeks, nose, and the like. In detail, it may be difficult to effectively adhere to the user's skin due to materials and variable characteristics of the device. Accordingly, the device may be operated in a state in which the device is not completely adhered to the user's skin, and the device may be separated from the user's skin due to the user's movement or vibration of the device during the operation thereof.

In this case, there is a problem that it is difficult for the user to check whether the device is adhered to the skin, and thus, it is difficult to effectively obtain a care effect through the device.

Therefore, a new mask capable of solving the above-described problem is required.

DISCLOSURE

Technical Problem

An embodiment is to provide a mask having variability and improved reliability.

In addition, the embodiment is to provide a mask capable of uniformly providing light energy, vibration, and microcurrent to a user's skin.

In addition, the embodiment is to provide a mask capable of selectively providing light energy, vibration, and microcurrent to the user's skin using a single device.

In addition, the embodiment is to provide a mask that can be effectively close-adhered to the user's skin.

In addition, the embodiment is to provide a mask capable of providing uniform vibration to the user's skin.

In addition, the embodiment is to provide a mask that can check whether the user's skin is closely adhered thereto.

Technical Solution

A mask according to an embodiment includes a first substrate, a first wiring disposed on the first substrate, a plurality of piezoelectric elements disposed on the first wiring, a second wiring disposed on the piezoelectric element, a second substrate disposed on the second wiring, a third wiring disposed on the first substrate and electrically insulated from the first wiring, and a plurality of light-emitting elements disposed between the first and second substrates and disposed on the third wiring, wherein the plurality of light-emitting elements are disposed on a region that overlaps a region between the plurality of piezoelectric elements in a vertical direction.

In addition, a skin care device according to an embodiment includes a main body in which one side thereof is open and an accommodation space is formed inside the open region and the above-described mask disposed in the open region and connected to the main body.

Advantageous Effects

A mask according to an embodiment may be varied according to a shape of curved skin of a user by a substrate having a variable material, a first base layer, a second base layer, or the like. Accordingly, the mask can be effectively adhered to the skin of the user, In addition, the mask according to the embodiment may include a plurality of piezoelectric elements spaced apart from each other, and the piezoelectric elements may be disposed at different intervals according to a curved shape of the skin. Accordingly, it is possible to provide vibration having a uniform intensity to the entire skin of the user who uses the mask.

In addition, the mask according to the embodiment may include a light-emitting element that provides light energy to the user's skin. In this case, the light-emitting element may be disposed in a region not overlapping the piezoelectric element, and accordingly, it is possible to prevent loss of light energy by the piezoelectric element.

In addition, the mask according to the embodiment may include the piezoelectric element and an electrode layer disposed on the light-emitting element. The electrode layer may effectively inject cosmetics or drugs by changing the electrical environment of the user's skin. In addition, the electrode layer may be formed with a line width of about 550 μm or less and a thickness of about 350 μm or less on the piezoelectric element and the light-emitting element, and accordingly, it is possible to minimize interference with the piezoelectric element and the light-emitting element, and the electrode layer can prevent the loss of vibration of the piezoelectric element and light of the light-emitting element.

In addition, in the mask according to the embodiment, the light-emitting element, the piezoelectric element, and the electrode layer may operate simultaneously. That is, the user can receive at once functions such as vibration, iontophoresis, and infrared rays using one mask.

In addition, the mask according to the embodiment may include a plurality of piezoelectric elements disposed in the entire region of the mask, and the piezoelectric elements may generate vibration over the entire region of the mask. In addition, the plurality of piezoelectric elements may be disposed at different intervals according to the curved shape of the skin. Accordingly, it is possible to provide vibration having a uniform intensity to the entire skin of the user who uses the mask.

In addition, the mask according to the embodiment may include a sensing unit, and the sensing unit may detect whether the mask is closely adhered to the skin. In detail, the mask may include a control unit connected to the sensing unit, and the control unit may detect whether the mask and the skin are closely adhered to each other based on a change in a capacitance value detected through the sensing unit. Accordingly, the mask according to the embodiment can provide information on whether the mask is spaced apart from the skin to the user, and the user can effectively care for the skin based on the information.

DESCRIPTION OF DRAWINGS

FIG. 1 is a front view of a mask according to a first embodiment.

FIG. 2 is an exploded perspective view of region A1 in FIG. 1.

FIG. 3 is a top view of the region A1 in FIG. 1.

FIG. 4 is a top view in which a third electrode is omitted from FIG. 3

FIG. 5 is a cross-sectional view taken along line A-A' of FIG. 3.

FIG. 6 is an enlarged view of region A2 in FIG. 5.

FIG. 7 is another exploded perspective view of the region A1 in FIG. 1.

FIG. 8 is a cross-sectional view of a mask of FIG. 7.

FIG. 9 is another cross-sectional view of the mask of FIG. 7.

FIG. 10 is a front view of a mask according to a second embodiment.

FIG. 11 is an exploded perspective view of region A3 in FIG. 10.

FIG. 12 is a top view of the region A3 in FIG. 10.

FIG. 13 is another top view of the region A3 in FIG. 10.

FIG. 14 is a cross-sectional view taken along line B-B' of FIG. 10.

FIG. 15 is an enlarged view of region A4 in FIG. 14.

FIGS. 16 and 17 are views illustrating a change in a capacitance value of a sensing unit according to whether the mask according to the second embodiment and the skin are in contact with each other.

FIG. 18 is a view illustrating that the mask according to the second embodiment includes a plurality of sensing units.

FIG. 19 is a view illustrating an example in which an indicator is disposed on the mask according to the embodiment.

FIGS. 20 and 21 are views illustrating an example in which a protrusion is disposed on the mask according to an embodiment.

FIG. 22 is a view illustrating a user wearing the mask according to the embodiment.

FIG. 23 is a view illustrating a skin care device to which the mask according to the embodiment is applied.

MODES OF THE INVENTION

Hereinafter, embodiments of the present invention will be described in detail with reference to the accompanying drawings.

However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may also include the plural forms unless specifically stated in the phrase, and may include at least one of all combinations that may be combined in A, B, and C when described in "at least one (or more) of A (and), B, and C".

In addition, in describing the elements of the embodiments of the present invention, the terms such as first, second, A, B, (A, and (b) may be used. These terms are only used to distinguish the elements from other elements, and the terms are not limited to the essence, order, or order of the elements. Further, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

Further, when described as being formed or disposed "on (over)" or "under (below)" of each element, the "on (over)" or "under (below)" may include not only when two elements are directly connected to each other, but also when one or more other elements are formed or disposed between two elements. Furthermore, when expressed as "on (over)" or "under (below)", it may include not only the upper direction but also the lower direction based on one element.

In addition, before describing the embodiments of the present invention, a first direction may refer to an x-axis direction shown in the drawings, and a second direction may be a different direction from the first direction. As an example, the second direction may refer to a y-axis direction shown in the drawing in a direction perpendicular to the first direction. In addition, a horizontal direction may refer to the first and second directions, and a vertical direction may refer to a direction perpendicular to at least one of the first and second directions. For example, the horizontal direction may refer to the x-axis and y-axis directions of the drawing, and the vertical direction may be a z-axis direction of the drawing and a direction perpendicular to the x-axis and y-axis directions.

First Embodiment

FIG. 1 is a front view of a mask according to a first embodiment, and FIG. 2 is an exploded perspective view of region A1 in FIG. 1. In addition, FIG. 3 is a top view of the region A1 in the mask according to the embodiment, and FIG. 4 is a top view in which a third electrode is omitted from FIG. 3. In addition, FIG. 5 is a cross-sectional view taken along line A-A' of FIG. 3, and FIG. 6 is an enlarged view of region A2 in FIG. 5.

Referring to FIGS. 1 to 6, a mask 1000 according to the embodiment may be provided in a predetermined size to cover a user's face and have a predetermined elasticity in order to be closely adhered to the user's face. The mask 1000 may include one surface in contact with the user's skin and the other surface opposite to the one surface, and the one surface of the mask 1000 may be made of a material that is harmless to the human body, so that it is harmless despite being in contact with the user's skin for a long time.

The mask 1000 may include at least one of an opening 1010 and a cutout portion 1020. In detail, the opening 1010 may be formed in a portion corresponding to the user's eyes or mouth. The opening 1010 is a region penetrating through one surface and the other surface of the mask 1000, and when the user wears the mask 1000, the user's eyes and mouth may be inserted into the opening 1010, and a region excluding the opening 1010 may be closely adhered to the user's face. In addition, the cutout portion 1020 may be formed in a portion corresponding to both cheek lines, chin, and the like, which are relatively curved in order to improve adhesion between the mask 1000 and the skin. The cutout portion 1020 may have a form in which one surface and the other surface of the mask 1000 are partially cut.

The region excluding the opening 1010 in the mask 1000 according to the embodiment may include a first substrate 110, a first wiring 210, a piezoelectric element 300, a second wiring 220, a second substrate 120, a light-emitting element 400, and an electrode layer 600.

The first substrate 110 may be transparent and include a material in consideration of moisture barrier properties, thermal stability, and the like. In addition, the first substrate 110 may include a material that has flexibility and varies according to a shape of the user's curved skin. As an example, the first substrate 110 may include a resin material such as polyethylene terephthalate (PET), polyethylene naphthalate (PEN), and polyimide (PI). The first substrate 110 may be provided in a form of a film.

The first substrate 110 may have a thickness of about 0.5 µm to about 5 µm or less. When the thickness of the first substrate 110 is less than about 0.5 µm, there may be a problem that a region of the first substrate 110 overlapping the components is struck by a weight of the components disposed on the first substrate 110, for example, the piezoelectric element 300. Accordingly, reliability of the first substrate 110 may be deteriorated, and a problem of alignment of the components disposed on the first substrate 110 may occur. In addition, when the thickness of the first substrate 110 exceeds about 5 µm, the overall thickness of the mask 1000 may be increased. Accordingly, there is a problem that the mask 1000 may not be efficiently varied according to the shape of the user's skin, and thus the mask 1000 does not effectively adhere to the user's skin. Preferably, the first substrate 110 may have a thickness of about 0.5 µm to about 3 µm. When the thickness of the first substrate 110 satisfies the above-described range, the first substrate 110 may be efficiently varied in a form corresponding to the user's skin and the overall thickness and weight of the mask 1000 may be reduced while maintaining reliability and alignment characteristics.

The first wiring 210 may be disposed on the first substrate 110. The first wiring 210 may include a conductive material. As an example, the first wiring 210 may include at least one metal of aluminum (Al), copper (Cu), silver (Ag), gold (Au), chromium (Cr), nickel (Ni), molybdenum (Mo), titanium (Ti), and alloys thereof. In addition, the first wiring 210 may include a non-metal such as carbon, and the like.

The first wiring 210 may be disposed on one surface of the first substrate 110 facing the user's skin. The first wiring 210 may be in direct contact with one surface of the first substrate 110 and extend in the first direction. The first wiring 210 may be formed on one surface of the first substrate 110 by a process such as deposition or printing.

The first wiring 210 may include a plurality of first sub-wirings 211 disposed on the first substrate 110. The plurality of first sub-wirings 211 may extend in the first direction and may be disposed to be spaced apart from each other in the second direction different from the first direction. The plurality of first sub-wirings 211 may be electrically connected to each other. Here, the second direction may be a direction different from the first direction and may be the vertical direction, for example, but the embodiment is not limited thereto.

A thickness of the first sub-wiring 211 may be about 2 µm to about 50 µm. In detail, the thickness of the first sub-wiring 211 may be about 2 µm to about 40 µm. When the thickness of the first sub-wiring 211 is less than about 2 µm, electrical characteristics may be deteriorated, and it may be difficult to form uniformly. In addition, when the thickness of the first sub-wiring 211 exceeds about 50 µm, the overall thickness of the mask 1000 may increase, and a manufacturing time of the first wiring 210 may increase. In addition, the thickness of the first sub-wiring 211 is too thick, and thus the stretchable characteristics may be deteriorated. Preferably, the thickness of the first sub-wiring 211 may be about 5 µm to about 35 µm or less in consideration of stretchable characteristics in the horizontal direction, reliability, and process efficiency.

In addition, a line width of the first sub-wiring 211 may be greater than the thickness of the first sub-wiring 211. For example, the line width of the first sub-wiring 211 may be about 50 µm to about 500 µm. In detail, the line width of the first sub-wiring 211 may be about 100 µm to about 450 µm. When the line width of the first sub-wiring 211 is less than about 50 µm, reliability may be deteriorated, and when the line width of the first sub-wiring 211 exceeds about 500 µm, an elongation may decrease and the stretchable characteristics may be deteriorated. Preferably, the line width of the first sub-wiring 211 may be about 100 µm to about 400 µm in consideration of the stretchable characteristics.

The first wiring 210 may have various shapes. For example, when viewed in a plane, each of the plurality of first sub-wirings 211 may have a linear shape extending in the first direction. Alternatively, when viewed in a plane, each of the plurality of first sub-wirings 211 may have a curved shape extending in the first direction. For example, each of the plurality of first sub-wirings 211 may be provided in a form in which a wavy pattern is repeated. In this case, the first sub-wiring 211 may have a curvature pattern of about 3 R to about 20 R (mm). Accordingly, when the mask 1000 is stretched or contracted in one direction, the first wiring 210 may have the stretchable characteristics and may not be cut. Preferably, the first sub-wiring 211 may have a curvature pattern of about 5 R to about 15 R (mm). Accordingly, the first wiring 210 may have more improved stretchable characteristics, thereby improving reliability. In addition, the first wiring 210 may have an elongation of about 10% to about 50%. Alternatively, when viewed in a plane, each of the plurality of first sub-wirings 211 may have a shape in which a pattern in which a straight line and a curve extending in the first direction are mixed is repeated. For example, when viewed from a plane, the first sub-wiring 211 positioned in a region overlapping a relatively curved region of the user's face may be provided in a curved shape, and the first sub-wiring 211 positioned in a region overlapping a relatively planar region may be provided in a straight line. Accordingly, when the mask 1000 is attached to the user's face, it is possible to solve a problem that the first wiring 210 is damaged due to deformation of the mask 1000. In addition, the first sub-wiring 211 may be provided in a form in which straight lines and curves are alternately disposed to reduce the amount of the first wires 210 disposed on the first substrate 110 and to improve the stretchable characteristics.

The piezoelectric element 300 may be disposed on the first substrate 110. In detail, the piezoelectric element 300 may be disposed on the first wiring 210 and electrically connected to the first wiring 210. The piezoelectric element 300 may include a ceramic material. As an example, the piezoelectric element 300 may include at least one of ZnO, AN, $LiNbO_4$, lead antimony stannate, lead magnesium tantalate, lead nickel tantalate, titanates, tungstates, zirconates, or lead including lead zirconate titanate [$Pb(Zr_xTi_{1-x})O_3$(PZT)], lead lanthanum zirconate titanate (PLZT), lead niobium Zirconate titanate (PNZT), $BaTiO_3$, $SrTiO_3$, lead magnesium niobate, lead nickel niobate, lead manganese niobate, lead zinc niobate, lead including lead titanate, barium, bismuth, or niobates of strontium.

The piezoelectric elements 300 may be disposed on the first wiring 210 in plural. In detail, a plurality of piezoelectric elements 300 may be disposed to be spaced apart from each other on the first sub-wiring 211. For example, the plurality of piezoelectric elements 300 may be disposed on one first sub-wiring 211, and the plurality of piezoelectric elements 300 may be spaced apart at equivalent intervals on the first sub-wiring 211. In addition, a piezoelectric element 300 disposed on one first sub-wiring 211 may or may not overlap a piezoelectric element 300 disposed on the first sub-wiring 211 closest to the one first sub-wiring 211 in the second direction. In addition, some of the piezoelectric elements 300 may be spaced apart at equivalent intervals, and the remaining piezoelectric elements 300 may not be disposed at equivalent intervals. For example, a space between the piezoelectric elements 300 may be disposed at equivalent intervals in a region overlapping a relatively flat region of the user's face surface. However, the space between the piezoelectric elements 300 may not be disposed at equivalent intervals in a region overlapping a relatively curved skin region. That is, the space between the piezoelectric elements 300 may be relatively narrow or large depending on the degree of curvature of the skin surface. Accordingly, the mask 1000 according to the embodiment may effectively provide vibration to the curved skin. In addition, the piezoelectric element 300 may be disposed on the entire region of the mask 1000 at predetermined intervals and generate evenly vibration in the entire region of the mask 1000.

The piezoelectric element 300 may overlap the first sub-wiring 211. In detail, a lower surface of the piezoelectric element 300 may overlap the first sub-wiring 211 in the vertical direction.

The piezoelectric element 300 may generate vibration by an applied current. For example, the piezoelectric element 300 may generate ultrasonic vibration by the applied current. In detail, the piezoelectric element 300 may generate ultrasonic vibration of about 1 MHz or less. In more detail, the piezoelectric element 300 may generate ultrasonic vibration of about 10 KHz to about 1 MHz. In more detail, the piezoelectric element 300 may generate ultrasonic vibration of about 100 KHz to about 800 KHz. The ultrasonic vibration generated by the piezoelectric element 300 vibrates in a direction of one surface of the mask 1000 and is transmitted to the user's skin, thereby massaging the user's skin.

A thickness of the piezoelectric element 300 may be about 1500 μm or less. In detail, the thickness of the piezoelectric element 300 may be about 1200 μm or less. Preferably, the thickness of the piezoelectric element 300 may be about 1000 μm or less. It is preferable that the thickness of the piezoelectric element 300 satisfies the above-described range in consideration of the overall thickness and variable characteristics of the mask 1000.

The piezoelectric element 300 may have various shapes. For example, the piezoelectric element 300 may have a polygonal column shape in which lower and upper surfaces are polygonal, and the lower and upper surfaces may have a circular column shape. In addition, one surface of the lower and upper surfaces of the piezoelectric member 300 may be a polygon and the other surface may have a pillar shape. As an example, an area of at least one of the lower surface and the upper surface of the piezoelectric element 300 may be about 100 $mm^2$ or less.

As described above, the piezoelectric element 300 may have various pillar shapes, and intensity of ultrasonic vibration and an oscillation direction of vibration generated according to the pillar shape may be controlled. In addition, the intensity of vibration transmitted to the user's skin may be adjusted according to a size, arrangement interval, arrangement density, and the like of the piezoelectric element 300.

The piezoelectric element 300 may generate various waves. As an example, the piezoelectric element 300 may generate at least one wave of a transverse wave in which a traveling direction of wave and a vibration direction of medium are perpendicular, and a longitudinal wave in which the traveling direction of wave and the vibration direction of medium are the same. In addition, the piezoelectric element 300 may multiple-resonate. For example, the piezoelectric element 300 may include at least one via hole and may multiple-resonate by the formed via holes. In this case, an upper area of the via holes may be about 10% to about 45% of an area of the upper surface of the piezoelectric element 300 for multiple resonance. In addition, when the piezoelectric element 300 multiple-resonates by the via holes, the number of multiple resonance frequency regions may correspond to the number of the via holes. That is, the piezoelectric element 300 may emit wavelengths of various frequency ranges as the number of the via holes increases in a set number range of via holes.

The second substrate 120 may be disposed on the piezoelectric element 300. The second substrate 120 may be transparent and include a material in consideration of moisture barrier properties, thermal stability, and the like. In addition, the second substrate 120 may include a material that has flexibility and varies according to a shape of the user's curved skin. As an example, the second substrate 120 may include a resin material such as polyethylene terephthalate (PET), polyethylene naphthalate (PEN), and polyimide (PI). The second substrate 120 may be provided in a form of a film. The second substrate 120 may be provided with the same material as the first substrate 110 and may have the same shape.

The second substrate 120 may have a thickness of about 0.5 μm to about 5 μm. When the thickness of the second substrate 120 is less than about 0.5 μm, there may be a problem that a region of the second substrate 120 overlapping the components is struck by a weight of the components disposed on the second substrate 120, for example, the piezoelectric element 300. Accordingly, reliability of the second substrate 120 may be deteriorated, and a problem of alignment of the components disposed on the second substrate 120 may occur. In addition, when the thickness of the second substrate 120 exceeds about 5 μm, the overall thickness of the mask 1000 may be increased. Accordingly, there is a problem that the mask 1000 may not be efficiently varied according to the shape of the user's skin, and thus the mask 1000 does not effectively adhere to the user's skin. Preferably, the second substrate 120 may have a thickness of about 0.5 μm to about 3 μm. When the thickness of the second substrate 120 satisfies the above-described range, the second substrate 120 may be efficiently varied in a form corresponding to the user's skin and the overall thickness and weight of the mask 1000 may be reduced while maintaining reliability and alignment characteristics. The second substrate 120 may have the same thickness as the first substrate 110.

The second wiring 220 may be disposed on the second substrate 120. The second wiring 220 may include a conductive material. For example, the second wiring 220 may include at least one metal of aluminum (Al), copper (Cu), silver (Ag), gold (Au), chromium (Cr), nickel (Ni), molybdenum (Mo), titanium (Ti), and alloys thereof. In addition, the second wiring 220 may include a non-metal such as carbon, and the like. The second wiring 220 may include the same material as the first wiring 210.

The second wiring 220 may be disposed on one surface of the second substrate 120 facing the piezoelectric element 300. That is, the second wiring 220 may be disposed on one surface opposite to the other surface of the second substrate 120 facing the user's skin. The second wiring 220 may be in direct contact with one surface of the second substrate 120 and may extend in a different direction from the first wiring 210. For example, the second wiring 220 may extend in the second direction perpendicular to the first direction in which the first wiring 210 extends. The second wiring 220 may be formed on one surface of the second substrate 120 by a process such as deposition or printing.

The second wiring 220 may include a plurality of second sub-wirings 221 disposed on the second substrate 120. The plurality of second sub-wirings 221 may extend in the second direction and may be spaced apart from each other in the first direction. The plurality of second sub-wirings 221 may be electrically connected to each other.

The second sub-wiring 221 may overlap the piezoelectric element 300. In detail, the second sub-wiring 221 may overlap the upper surface of the piezoelectric element 300 in the vertical direction.

The first wiring 210 and the second wiring 220 may be disposed to cross each other. In detail, when viewed in a plane, the first sub-wiring 211 and the second sub-wiring 221 may be disposed to cross each other in a mesh shape, and an open region OA in which the electrodes 210 and 220 are not disposed may be formed between the sub-wirings 211 and 221.

A thickness of the second sub-wiring 221 may be about 2 μm to about 50 μm. In detail, the thickness of the second sub-wiring 221 may be about 2 μm to about 40 μm. When the thickness of the second sub-wiring 221 is less than about 2 μm, electrical characteristics may be deteriorated, and it may be difficult to form uniformly. In addition, when the thickness of the second sub-wiring 221 exceeds about 50 μm, the overall thickness of the mask 1000 may increase, and a manufacturing time of the second wiring 220 may increase. In addition, the thickness of the second sub-wiring 221 is too thick, and thus stretchable characteristics may be deteriorated. Preferably, the thickness of the second sub-wiring 221 may be about 30 μm or less in consideration of stretchable characteristics in the horizontal direction, reliability, and process efficiency. The thickness of the second sub-wiring 221 is provided equal to the thickness of the first sub-wiring 211, so that process efficiency may be improved.

In addition, a line width of the second sub-wiring 221 may be greater than the thickness of the second sub-wiring 221. For example, the line width of the second sub-wiring 221 may be about 50 μm to about 500 μm. In detail, the line width of the second sub-wiring 221 may be about 100 μm to about 450 μm. When the line width of the second sub-wiring 221 is less than about 50 μm, reliability may be deteriorated, and when the line width of the second sub-wiring 221 exceeds about 500 μm, an elongation may decrease and the stretchable characteristics may be deteriorated. Preferably, the line width of the second sub-wiring 221 may be about 100 μm to about 400 μm in consideration of the stretchable characteristics. The line width of the second sub-wiring 221 is provided equal to the line width of the first sub-wiring 211, so that process efficiency may be improved.

The second wiring 220 may have various shapes. For example, when viewed in a plane, each of the plurality of second sub-wirings 221 may have a linear shape extending in the second direction. Alternatively, when viewed in a plane, each of the plurality of second sub-wirings 221 may have a curved shape extending in the second direction. For example, each of the plurality of second sub-wirings 221 may be provided in a form in which a wavy pattern is repeated. In this case, the second sub-wiring 221 may have a curvature pattern of about 3 R to about 20 R (mm). Accordingly, when the mask 1000 is stretched or contracted in one direction, the second wiring 220 may have the stretchable characteristics and may not be cut. Preferably, the second sub-wiring 221 may have a curvature pattern of about 5 R to about 15 R (mm). Accordingly, the second wiring 220 may have more improved stretchable characteristics, thereby improving reliability. In addition, the second wiring 220 may have an elongation of about 10% to about 50%. Alternatively, when viewed in a plane, each of the plurality of second sub-wirings 221 may have a shape in which a pattern in which a straight line and a curve extending in the second direction are mixed is repeated. For example, when viewed in a plane, the second sub-wiring 221 positioned in a region overlapping a relatively curved region of the user's face may be provided in a curved shape, and the second sub-wiring 221 positioned in a region overlapping a relatively planar region may be provided in a straight line. Accordingly, when the mask 1000 is attached to the user's face, it is possible to solve a problem that the second wiring 220 is damaged due to deformation of the mask 1000. In addition, the second sub-wiring 221 may be provided in a form in which straight lines and curves are alternately disposed to reduce the amount of the first wiring 210 disposed on the second substrate 120 and to improve the stretchable characteristics. In this case, it is preferable that the second wiring 220 has the same shape as the first wiring 210 in consideration of the stretchable characteristic of the mask 1000. It is preferable that the first wiring 210 and the second wiring 220 disposed in the same region have the same shape as each other.

In addition, although not shown in the drawing, the second wiring 220 may extend on the second substrate 120 in the same direction as the first wiring 210. That is, the second wiring 220 may extend in the same first direction as the first wiring 210.

The mask 1000 according to the embodiment may include a first base layer 510. The first base layer 510 may be disposed under the first substrate 110. The first base layer 510 may be disposed on the other surface opposite to one surface of the first substrate 110. The first base layer 510 may be disposed in direct contact with the other surface of the first substrate 110.

The first base layer 510 may include a material harmless to the human body. In addition, the first base layer 510 may include a soft and elastic material. For example, the first base layer 510 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the first base layer 510 may include a silicone elastomer among them that is relatively light, can minimize irritation upon contact with the user's skin, and has a predetermined elasticity.

The first base layer 510 may be disposed to cover the entire region of the other surface of the first substrate 110. That is, when viewed in a plane, a plan area of the first base layer 510 may correspond to an area of the other surface of the first substrate 110. In addition, the plan area of the first base layer 510 may be greater than the area of the other surface of the first substrate 110. Accordingly, the first base layer 510 may be disposed surrounding a side surface of the first substrate 110. The first base layer 510 may prevent the other surface of the first substrate 110 from being exposed to the outside. In addition, the first base layer 510 may reflect wavelengths emitted from the piezoelectric element 300 in a direction of one surface of the mask 1000. That is, the first base layer 510 may be a reflective layer. To this end, a thickness of the first base layer 510 may be about 50 μm to about 1 mm. When the thickness of the first base layer 510 is less than about 50 μm, the thickness of the first base layer 510 is relatively small, so that the first substrate 110 may not be effectively protected. In addition, when the thickness of the first base layer 510 exceeds about 1 mm, a thickness of the entire mask 1000 may be increased, and most of the wavelengths emitted from the piezoelectric element 300 in a direction of the first substrate 110 pass through the first base layer 510, and are reflected by the first base layer 510, so that the amount of reflection in the direction of one surface of the mask 1000 may be small. In addition, a required thickness of a second base layer 520 to be described later may be increased for reflection in the direction of one surface of the mask 1000, and a region of wavelengths generated from the piezoelectric element 300 is high for reflection, and thus it may not be suitable for use in the mask 1000. Therefore, it is preferable that the thickness of the first base layer 510 satisfies the above-described range in order to prevent the above problems. More preferably, the thickness of the first base layer 510 may be about 100 μm to about 700 μm. That is, it is preferable that the first base layer 510 has a thickness range of about 100 μm to about 700 μm in consideration of reliability, reflective properties, and the thickness and weight of the mask 1000 to be manufactured. In addition, the first base layer 510 may have pores or the like formed therein in order to effectively reflect the wavelengths generated from the piezoelectric element 300. In addition, one surface of the first base layer 510 facing the piezoelectric element 300 may include at least one groove concave from the one surface toward the other surface opposite to the one surface. The groove may be disposed at a position overlapping the piezoelectric element 300 in the vertical direction and may be filled with air or the like to reflect the wavelengths of the piezoelectric element 300 upward, for example, toward the second substrate.

The mask 1000 according to the embodiment may include the second base layer 520. The second base layer 520 may be disposed on the second substrate 120. The second base layer 520 may be disposed on the other surface opposite to the one surface of the second substrate 120. The second base layer 520 may be disposed in direct contact with the other surface of the second substrate 120.

The second base layer 520 is a portion that may be in contact with the skin while facing the user's skin, and may include a material harmless to the human body. In addition, the second base layer 520 may include a soft and elastic material. For example, the second base layer 520 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second base layer 520 may include a silicone elastomer among them that is relatively light, can minimize irritation upon contact with the user's skin, and has a predetermined elasticity. That is, the second base layer 520 may be provided with the same material as the first base layer 510.

The second base layer 520 may be disposed to cover the entire region of the other surface of the second substrate 120. That is, when viewed in a plane, a plan area of the second base layer 520 may correspond to an area of the other surface of the second substrate 120. In addition, the plan area of the second base layer 520 may be greater than the area of the other surface of the second substrate 120. Accordingly, the second base layer 520 may be disposed surrounding a side surface of the second substrate 120. The second base layer 520 may prevent the other surface of the second substrate 120 from being exposed to the outside. In addition, the second base layer 520 may pass through the wavelengths emitted from the piezoelectric element 300 in the direction of one surface of the mask 1000 to transmit the wavelengths to the user's skin. That is, the second base layer 520 may be a transmission layer. A thickness of the second base layer 520 may vary depending on an impedance of the second base layer 520 and a driving frequency of the piezoelectric element 300. As an example, when the driving frequency of the piezoelectric element 300 is about 1 MHz or less, the thickness of the second base layer 520 may be about 50 μm to about 1 mm. When the thickness of the second base layer 520 is less than about 50 µm, the thickness of the second base layer 520 is relatively small, so that the second substrate 120 may not be effectively protected. In addition, when the thickness of the second base layer 520 exceeds about 1 mm, the thickness of the entire mask 1000 may be increased. It is preferable that the thickness of the second base layer 520 satisfies the above-described range in order to effectively pass through the wavelengths emitted from the piezoelectric element 300. Preferably, the thickness of the second base layer 520 may have a thickness range of 100 µm to about 700 µm in consideration of reliability, transmission characteristics, and the thickness and weight of the mask 1000 to be manufactured. In addition, the thickness of the second base layer 520 may be equal to or greater than the thickness of the first base layer 510 within the above-described range. Accordingly, the wavelengths emitted from the piezoelectric element 300 toward the second substrate 120 may be prevented or minimized from being reflected on the second base layer 520. Therefore, the wavelengths emitted from the piezoelectric element 300 may pass through the second substrate 120 and the second base layer 520 to be effectively transmitted to the user's skin.

The mask 1000 according to the embodiment may include the light-emitting element 400. The light-emitting element 400 may be disposed on the first substrate 110. The light-emitting element 400 may be disposed between the first substrate 110 and the second substrate 120. In detail, the light-emitting element 400 may be disposed between the plurality of piezoelectric elements 300. That is, the light-emitting element 400 may be disposed in a region vertically overlapping the open region OA between the sub-wirings 211 and 221 of the first and second wires 210 and 220.

The light-emitting element 400 may be disposed on a third wiring 230 disposed on one surface of the first substrate 110 and may be electrically connected to the third wiring 230. The third wiring 230 may include a conductive material. As an example, the third wiring 230 may include at least one metal of aluminum (Al), copper (Cu), silver (Ag), gold (Au), chromium (Cr), nickel (Ni), molybdenum (Mo), titanium (Ti), and alloys thereof. In addition, the third wiring 230 may include a non-metal such as carbon, and the like.

The third wiring 230 may include a plurality of third sub-wirings 231 disposed on the first substrate 110. The plurality of third sub-wirings 231 may be electrically connected to each other. In addition, the third wiring 230 may be electrically insulated from the first wiring 210. In detail, the plurality of third sub-wirings 231 may be insulated from the first sub-wirings 211 disposed on the first substrate 110. In addition, the third wiring 230 may be electrically insulated from the second wiring 220. In detail, the third sub-wirings 231 may be insulated from the second sub-wirings 221.

The light-emitting elements 400 may be disposed on the third wiring 230 A in plural. In detail, the plurality of light-emitting elements 400 may be disposed to be spaced apart from each other on the third sub-wiring 231. For example, the plurality of light-emitting elements 400 may be disposed on one third sub-wiring 231 at equivalent intervals.

The light-emitting element 400 may emit light in the direction of one surface of the mask 1000. That is, the light-emitting element 400 may emit light in a direction of the user's skin.

The light-emitting element 400 may emit light in at least one wavelength region of visible light and infrared light. For example, the light-emitting element 400 may emit light in a visible light region of about 380 nm to about 700 nm. In detail, the light-emitting element 400 may be a light-emitting element having the greatest intensity of light in a wavelength region of about 600 nm to about 700 nm in the emitted light. That is, the light-emitting element 400 may be a light-emitting element that emits red light. Accordingly, red light may be irradiated onto the skin of the user wearing the mask 1000, and inflammatory diseases such as acne on the user's skin may be effectively treated. In addition, the light-emitting element 400 may emit light in an infrared region of about 700 nm to about 1500 nm. In detail, the light-emitting element 400 may be a light-emitting element having the greatest intensity of light in a wavelength region of about 800 nm to 900 nm in the emitted light. That is, the light-emitting element 400 may be a light-emitting element emitting near-infrared rays. Accordingly, infrared light may be irradiated to the skin of the user wearing the mask 1000, pore expansion, skin disinfection, and treatment effects of the user may be expected, and skin aging may be prevented and treated. In addition, the infrared light may improve the blood circulation of the user's face and increase the absorption of cosmetics or drugs applied to the user's face.

As described above, the light-emitting element 400 may include at least one of a visible light-emitting element and an infrared light-emitting element. In this case, when the light-emitting element 400 according to the embodiment includes both a visible light-emitting element and an infrared light-emitting element, the light-emitting elements may be arranged regularly. For example, the light-emitting element 400 may be provided in a form in which the visible light-emitting element and the infrared light-emitting element are alternately disposed. Accordingly, red light and near-infrared light may be evenly incident on the entire area of the wearer's face.

Alternatively, the visible light-emitting element and the infrared light-emitting element may be disposed at different ratios. As an example, in a region of the mask 1000 that overlaps a region prone to occur inflammatory diseases such as acne, the visible light-emitting element may be disposed at a higher ratio than the infrared light-emitting element. In addition, the infrared light-emitting element may be disposed at a higher ratio than the visible light-emitting element in an area of the mask 1000 that overlaps a region where wrinkles are likely to occur, such as forehead or eye rims. Accordingly, the user may effectively manage the facial skin through the mask 1000.

In addition, although not shown in the drawings, the second substrate 120 may include a through-hole (not shown) formed in a region corresponding to the light-emitting element 400. The through-hole may be a hole passing through one surface and the other surface of the second substrate 120. A width in a horizontal direction of the through-hole may be equal to or greater than a width in a horizontal direction of the light-emitting element. However, the embodiment is not limited thereto, and the width of the through-hole may be changed depending on a directivity angle of the light-emitting element 400. That is, as the second substrate 120 includes the through-hole, it is possible to minimize the loss of light emitted from the light-emitting element 400 by the second substrate 120 and to maximize an amount of light incident on the user's skin.

The mask 1000 according to the embodiment may include the first protective layer 551. The first protective layer 551 may be disposed between the first substrate 110 and the second substrate 120. The first protective layer 551 may be disposed in direct contact with one surface of the first substrate 110 and one surface of the second substrate 120.

The first protective layer 551 may include a material having softness and elasticity. For example, the first protective layer 551 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The first protective layer 551 may be preferable to include a silicone elastomer among them that is relatively light, can minimize irritation upon contact with the user's skin, and has a predetermined elasticity.

The first protective layer 551 may be disposed between the first substrate 110 and the second substrate 120 to protect the piezoelectric element 300 and the light-emitting element 400. In detail, the first protective layer 551 may be disposed in a region between the substrates 110 and 120 to surround the piezoelectric element 300 and the light-emitting element 400 to protect the components. In addition, the first protective layer 551 may be connected to the first base layer 510 and the second base layer 520. That is, the first base layer 510, the second base layer 520, and the first protective layer 551 may be integrally formed to be physically connected and support a component disposed therein.

In more detail, the piezoelectric element 300 may include a first electrode 310 disposed on a lower surface. The first electrode 310 may be disposed in an area of about 80% or more of the entire area of the lower surface of the piezoelectric element 300 in consideration of electrical characteristics. In detail, the first electrode 310 may be disposed in an area of about 90% of the entire area of the lower surface of the piezoelectric element 300. In addition, the first electrode 310 may be disposed on the entire region of the lower surface of the piezoelectric element 300. However, there is a problem that it is difficult to form the first electrode 310 while covering the entire region in the electrode formation process, and thus it may be preferable that a ratio occupied by the first electrode 310 satisfies the above-described range.

The first electrode 310 may include a conductive material. As an example, the first electrode 310 may include a metal material. In detail, the first electrode 310 may include at least one metal of aluminum (Al), copper (Cu), silver (Ag), gold (Au), chromium (Cr), nickel (Ni), molybdenum (Mo), titanium (Ti), and alloys thereof.

The first electrode 310 may be disposed facing the first wiring 210 and may be electrically connected to the first wiring 210. In detail, a first bonding layer 251 may be disposed between the first electrode 310 and the first wiring 210, and the first electrode 310 and the first wiring 210 may be physically and electrically connected by the first bonding layer 251. In this case, an overlapping ratio between the first bonding layer 251 and the first wiring 210 may be about 20% or more in consideration of physical and electrical connection characteristics.

The first bonding layer 251 may include at least one metal of aluminum (Al), copper (Cu), silver (Ag), gold (Au), chromium (Cr), nickel (Ni), molybdenum (Mo), titanium (Ti), and alloys thereof. The first bonding layer 251 may be disposed between the first electrode 310 and the first wiring 210 to serve as a conductive adhesive. As an example, the first bonding layer 251 may be applied in a form of a paste on the first wiring 210, and the piezoelectric element 300 including the first electrode 310 may be disposed on the first bonding layer 251. Accordingly, the piezoelectric element 300 may be physically and electrically connected to the first wiring 210.

In addition, the piezoelectric element 300 may include a second electrode 320 disposed on an upper surface thereof. The second electrode 320 may be disposed in an area of about 80% or more of the entire area of the upper surface of the piezoelectric element 300 in consideration of electrical characteristics. In detail, the second electrode 320 may be disposed in an area of about 90% of the entire area of the upper surface of the piezoelectric element 300. In addition, the second electrode 320 may be disposed on the entire region of the lower surface of the piezoelectric element 300. However, there is a problem in that it is difficult to form the second electrode 320 while covering the entire region in the electrode formation process, and thus it may be preferable that a ratio occupied by the second electrode 320 satisfies the above-described range.

The second electrode 320 may include a conductive material. As an example, the second electrode 320 may include a metal material. In detail, the second electrode 320 may include at least one metal of aluminum (Al), copper (Cu), silver (Ag), gold (Au), chromium (Cr), nickel (Ni), molybdenum (Mo), titanium (Ti), and alloys thereof.

The second electrode 320 may be disposed facing the second wiring 220 and may be electrically connected to the second wiring 220. In detail, a second bonding layer 252 may be disposed between the second electrode 320 and the second wiring 220, and the second electrode 320 and the second wiring 220 may be physically and electrically connected by the second bonding layer 252. In this case, an overlapping ratio between the second bonding layer 252 and the second wiring 220 may be about 20% or more in consideration of physical and electrical connection characteristics.

The second bonding layer 252 may include at least one metal of aluminum (Al), copper (Cu), silver (Ag), gold (Au), chromium (Cr), nickel (Ni), molybdenum (Mo), titanium (Ti), and alloys thereof. The second bonding layer 252 may be disposed between the second electrode 320 and the second wiring 220 to serve as a conductive adhesive. As an example, the second bonding layer 252 may be applied in the form of the paste on the second wiring 220, and the piezoelectric element 300 including the second electrode 320 may be disposed on the second bonding layer 252. Accordingly, the piezoelectric element 300 may be physically and electrically connected to the second wiring 220, and the first substrate 110 and the second substrate 120 may be spaced apart from each other at a predetermined interval.

The first bonding layer 251 may be provided with the same thickness as the second bonding layer 252 to improve the variability of the mask 1000. In addition, the thickness of the first bonding layer 251 may be different from the thickness of the second bonding layer 252. In detail, the thickness of the first bonding layer 251 may be greater than the thickness of the second bonding layer 252. Accordingly, the wavelengths emitted from the piezoelectric element 300 toward the first substrate 110 may be reflected by the first bonding layer 251 to move toward the second substrate 120.

In addition, the mask 1000 may further include a third bonding layer (not shown). The third bonding layer may be disposed on the other surface of the first substrate 110. That is, the third bonding layer may be disposed between the other surface of the first substrate 110 and the first base layer 510. Accordingly, the wavelengths emitted from the piezoelectric element 300 toward the first substrate 110 may be reflected by the third bonding layer to move toward the second substrate 120. Accordingly, it is possible to minimize the loss of wavelengths emitted from the piezoelectric element 300.

Thereafter, as described above, the first protective layer 551 may be filled in a space between the first substrate 110 and the second substrate 120. Accordingly, the first protective layer 551 may be disposed surrounding the piezoelectric element 300 and the light-emitting element 400, and it is possible to prevent the piezoelectric element 300, the light-emitting element 400, the first wiring 210, and the second wiring 220 from being directly exposed to an external environment.

The mask 1000 according to the embodiment may include the electrode layer 600. The electrode layer 600 may be disposed on the second base layer 520. In detail, the electrode layer 600 may be disposed on one surface of the second base layer 520 facing the user's skin. The electrode layer 600 may overlap at least one of the piezoelectric element 300 and the light-emitting element 400 based on the vertical direction.

The electrode layer 600 may include a conductive material. As an example, the electrode layer 600 may include at least one metal of aluminum (Al), copper (Cu), silver (Ag), gold (Au), chromium (Cr), nickel (Ni), molybdenum (Mo), titanium (Ti), and alloys thereof.

The electrode layer 600 may include a plurality of sub-electrodes 601. The plurality of sub-electrodes 601 may be electrically connected to each other while crossing in a mesh shape on the second base layer 520.

The electrode layer 600 may change the electrical environment of the skin by forming a potential difference in the user's skin. In detail, the electrode layer 600 may allow a microcurrent to flow through the user's skin to penetrate an ionic material included in the cosmetics or drugs positioned between the mask 1000 and the skin into the user's skin. That is, the cosmetics or drugs may penetrate into the user's skin by the electric repulsive force formed by the electrode layer 600.

To this end, a line width of the electrode layer 600 may be about 550 μm or less. In addition, a thickness of the electrode layer 600 may be about 350 μm or less. When the line width and thickness of the electrode layer 600 are greater than the above-described range, light emitted from the light-emitting element 400 may be reflected by the electrode layer 600 and re-incident into the mask 1000. In addition, the waves generated from the piezoelectric element 300 may not effectively move in the direction of one surface of the mask 1000 by the electrode layer 600. Therefore, it may be preferable that the line width and thickness of the electrode layer 600 satisfy the above-described range. Further, it may be more preferable that each of the line width and thickness of the electrode layer 600 is about 500 μm, about 300 μm or less in consideration of reliability, light efficiency of the light-emitting element 400, movement of the waves emitted from the piezoelectric element 300, and iontophoresis characteristics.

In addition, although not shown in the drawings, a plurality of protrusions (not shown) may be further disposed on the one surface of the second base layer 520. The protrusion may be disposed on the outermost surface of the mask 1000 in contact with the user's skin. The protrusions may be disposed in a form of a plurality of points spaced apart from each other on the one surface of the second base layer 520 and in a form of a line connected to each other. The protrusion may be disposed to be spaced apart from the electrode layer 600 and include a material harmless to the human body. The protrusion may form a predetermined space between the one surface of the second base layer 520 and the user's skin when the user wears the mask 1000. Accordingly, it is possible to prevent cosmetics or drugs between the mask 1000 and the skin from being pushed out to an edge region of the mask 1000 by the pressure generated when the mask 1000 is worn and/or the vibration generated from the piezoelectric element 300. That is, the protrusion may serve as a partition wall preventing cosmetics or drugs from getting out of the mask 1000. Therefore, the user may effectively inject cosmetics or drugs into the skin using the mask 1000.

FIG. 7 is another exploded perspective view of region A1 in FIG. 1, and FIG. 8 is a cross-sectional view of the mask of FIG. 7, and FIG. 9 is another cross-sectional view of the mask of FIG. 7.

In the description of FIGS. 7 to 9, descriptions of the same configurations as those of the masks of FIGS. 1 to 6 are omitted, and the same reference numerals are assigned to the same as or similar to configurations.

Referring to FIGS. 7 and 8, the mask 1000 according to the embodiment may have a multiple layer structure, and the light-emitting element 400 and the piezoelectric element 300 may be disposed on different layers. The light-emitting element 400 may be disposed on the other surface of the second substrate 120. In detail, the third wiring 230 may be disposed on the other surface of the second substrate 120, and the light-emitting element 400 may be disposed on the third wiring 230. The light-emitting element 400 may be disposed on a region vertically overlapping the open region OA between the sub-wirings 211 and 221 of the first and second wires 210 and 220 on the second substrate 120.

The first protective layer 551 may be disposed between the first substrate 110 and the second substrate 120. The first protective layer 551 may be disposed between the first substrate 110 and the second substrate 120 to surround the piezoelectric element 300. The first protective layer 551 may be spaced apart from the light-emitting element 400 and may prevent the piezoelectric element 300, the first wiring 210, and the second wiring 220 from being exposed to the external environment.

The second base layer 520 may be disposed on the second substrate 120. The second base layer 520 may be disposed on the other surface of the second substrate 120. The second base layer 520 may be disposed on the second substrate 120 to surround the light-emitting element 400. The second base layer 520 may prevent the light-emitting element 400 and the third wiring 230 from being exposed to the external environment.

The second base layer 520 may have a height corresponding to the light-emitting element 400. In addition, the second base layer 520 may be equal to or greater than the thickness of the first base layer 510 in order to effectively pass through the wavelengths emitted from the piezoelectric element 300 in the direction of one surface of the mask 1000. Have. Accordingly, the waves generated from the piezoelectric element 300 may effectively move in the direction of one surface of the mask 1000, and light emitted from the light-emitting element 400 may be emitted in a direction of the electrode layer 600, for example in the direction of the user's skin. In addition, as the light-emitting element 400 is disposed closer to one surface of the second base layer 520, it is possible to prevent and minimize the light emitted from the light-emitting element 400 from being lost inside the mask 1000.

The second base layer 520 may be connected to the first protective layer 551 and the first protective layer 551. That is, the first base layer 510, the second base layer 520, and the first protective layer 551 may be integrally formed to be physically connected and may support a component disposed therein.

Referring to FIG. 9, the mask 1000 according to the embodiment may have a multiple layer structure and may include a third substrate 130 disposed on the second substrate 120 and a second protective layer 552 disposed on the third substrate 130.

The third substrate 130 may be transparent and include a material in consideration of moisture barrier properties, thermal stability, and the like. In addition, the third substrate 130 may include a material that has flexibility and varies according to a shape of the user's curved skin. As an example, the third substrate 130 may include a resin material such as polyethylene terephthalate (PET), polyethylene naphthalate (PEN), and polyimide (PI). The third substrate 130 may be provided in a form of a film. The third substrate 130 may be provided with the same material as the first substrate 110 and the second substrate 120, and may have the same shape.

The second base layer 520 may be disposed under the third substrate 130. That is, the second base layer 520 may be disposed between the second substrate 120 and the third substrate 130. The second base layer 520 may serve to physically connect the second substrate 120 and the third substrate 130. In addition, the second base layer 520 may have a thickness greater than that of the first base layer 510 or the same thickness in order to effectively pass through the wavelengths emitted from the piezoelectric element 300 in the direction of one surface of the mask 1000.

The light-emitting element 400 may be disposed on the third substrate 130. In detail, the third wiring 230 may be disposed on one surface of the third substrate 130 facing the user's skin, and the light-emitting element 400 may be disposed on the third wiring 230.

The second protective layer 552 may be disposed on the third substrate 130. The second protective layer 552 may be disposed on one surface of the third substrate 130. The third substrate 130 may include a material harmless to the human body. The second protective layer 552 may include a soft and elastic material. For example, the second protective layer 552 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second protective layer 552 may include a silicone elastomer among them that is relatively light, can minimize irritation upon contact with the user's skin, and has a predetermined elasticity. That is, the second protective layer 552 may be provided with the same material as the second base layer 520, the first base layer 510, and the first protective layer 551, so that it is possible to effectively pass through the wavelengths emitted from the piezoelectric element 300.

The second protective layer 552 may be disposed on the third substrate 130 to surround the light-emitting element 400. The second protective layer 552 may have a thickness corresponding to the light-emitting element 400. In addition, the second protective layer 552 may be provided with a thickness corresponding to the second base layer 520 so that the waves generated from the piezoelectric element 300 may effectively move. The second protective layer 552 may prevent the light-emitting element 400 and the third wiring 230 from being exposed to the external environment.

In addition, the electrode layer 600 may be disposed on the second protective layer 552. The electrode layer 600 may be disposed on the outermost layer of the mask 1000. In detail, the electrode layer 600 may be disposed on one surface of the second protective layer 552 facing the user's skin. The electrode layer 600 may overlap at least one of the piezoelectric element 300 and the light-emitting element 400 in the vertical direction.

In addition, the second protective layer 552 may be connected to the first base layer 510, the second base layer 520, and the first protective layer 551. That is, the second protective layer 552 may be integrally formed with the first base layer 510, the second base layer 520, and the first protective layer 551 to be physically connected and support a component disposed therein.

Accordingly, the waves generated from the piezoelectric element 300 may effectively move in the direction of one surface of the mask 1000, and light emitted from the light-emitting element 400 may be emitted in a direction of the electrode layer 600, for example in the direction of the user's skin. In addition, as the light-emitting element 400 is disposed closer to one surface of the second base layer 520, it is possible to prevent and minimize the light emitted from the light-emitting element 400 from being lost inside the mask 1000. In addition, as a space between the light-emitting element 400 and the piezoelectric element 300 is sufficiently separated by the third substrate 130 and the second base layer 520, the piezoelectric element 300 may minimize the influence of heat emitted from the light-emitting element 400. Accordingly, the mask 1000 according to the embodiment may have improved reliability.

Second Embodiment

FIG. 10 is a front view of a mask according to a second embodiment, and FIG. 11 is an exploded perspective view of region A3 in FIG. 10. In addition, FIG. 12 is a top view of the region A3 in FIG. 10, and FIG. 13 is another top view of the region A3 in FIG. 10. In addition, FIG. 14 is a cross-sectional view taken along line B-B' of FIG. 12, and FIG. 15 is an enlarged view of region A4 in FIG. 14.

In the description of FIGS. 10 to 15, the same reference numerals are assigned to configurations the same as or similar to those of the mask of the first embodiment, and the same or similar configurations may be selectively applied to the second embodiment with reference to the first embodiment.

Referring to FIGS. 10 to 15, a mask 1000A according to the second embodiment may be provided in a predetermined size capable of covering the user's face and may have a predetermined elasticity in order to be closely adhered to the user's face. The mask 1000A may include at least one of an opening 1010 and a cutout portion 1020. In detail, the opening 1010 may be formed in a portion corresponding to the user's eyes or mouth. In addition, the cutout portion 1020 may be formed in a portion corresponding to both cheek lines, chin, and the like, which are relatively curved in order to improve adhesion between the mask 1000A and the skin.

A region excluding the opening 1010 in the mask 1000A according to the second embodiment may include a first substrate 110, a first wiring 210, a piezoelectric element 300, a second wiring 220, a second substrate 120, a first base layer 510, a second base layer 520, and a sensing unit 700.

The first substrate 110 may be transparent and include a material in consideration of moisture barrier properties, thermal stability, and the like. In addition, the first substrate 110 may include a material that has flexibility and varies according to a shape of the user's curved skin. As an example, the first substrate 110 may include a resin material such as polyethylene terephthalate (PET), polyethylene naphthalate (PEN), and polyimide (PI). The first substrate 110 may be provided in a form of a film.

The first substrate 110 may have a thickness of about 0.5 µm to about 5 µm or less. When the thickness of the first substrate 110 is less than about 0.5 µm, there may be a problem that a region of the first substrate 110 overlapping the components is struck by a weight of the components disposed on the first substrate 110, for example, the piezoelectric element 300. Accordingly, reliability of the first substrate 110 may be deteriorated, and a problem of alignment of the components disposed on the first substrate 110 may occur. In addition, when the thickness of the first substrate 110 exceeds about 5 µm, the overall thickness of the mask 1000A may be increased. Accordingly, there is a problem that the mask 1000A may not be efficiently varied according to the shape of the user's skin, and thus the mask 1000A does not effectively adhere to the user's skin. Preferably, the first substrate 110 may have a thickness of about 0.5 µm to about 3 µm. When the thickness of the first substrate 110 satisfies the above-described range, the first substrate 110 may be efficiently varied in a form corresponding to the user's skin and the overall thickness and weight of the mask 1000A may be reduced while maintaining reliability and alignment characteristics.

The first wiring 210 may be disposed on the first substrate 110. The first wiring 210 may be electrically connected to the piezoelectric element 300. The first wiring 210 may include a conductive material. As an example, the first wiring 210 may include at least one metal of aluminum (Al), copper (Cu), silver (Ag), gold (Au), chromium (Cr), nickel (Ni), molybdenum (Mo), titanium (Ti), and alloys thereof. In addition, the first wiring 210 may include a non-metal such as carbon, and the like.

The first wiring 210 may be disposed on one surface of the first substrate 110 facing the user's skin. The first wiring 210 may be in direct contact with one surface of the first substrate 110 and extend in the first direction. The first wiring 210 may be formed on one surface of the first substrate 110 by a process such as deposition or printing.

The first wiring 210 may include a plurality of first sub-wirings 211 disposed on the first substrate 110. The plurality of first sub-wirings 211 may extend in the first direction and may be disposed to be spaced apart from each other in the second direction different from the first direction. The plurality of first sub-wirings 211 may be electrically connected to each other. Here, the second direction may be a direction different from the first direction and may be the vertical direction, for example, but the embodiment is not limited thereto.

A thickness of the first sub-wiring 211 may be about 2 µm to about 50 µm. In detail, the thickness of the first sub-wiring 211 may be about 2 µm to about 40 µm. When the thickness of the first sub-wiring 211 is less than about 2 µm, electrical characteristics may be deteriorated, and it may be difficult to form uniformly. In addition, when the thickness of the first sub-wiring 211 exceeds about 50 µm, the overall thickness of the mask 1000 may increase, and a manufacturing time of the first wiring 210 may increase. In addition, the thickness of the first sub-wiring 211 is too thick, and thus the stretchable characteristics may be deteriorated. Preferably, the thickness of the first sub-wiring 211 may be about 5 µm to about 35 µm or less in consideration of stretchable characteristics in the horizontal direction, reliability, and process efficiency.

In addition, a line width of the first sub-wiring 211 may be greater than the thickness of the first sub-wiring 211. For example, the line width of the first sub-wiring 211 may be about 50 µm to about 500 µm. In detail, the line width of the first sub-wiring 211 may be about 100 µm to about 450 µm. When the line width of the first sub-wiring 211 is less than about 50 µm, reliability may be deteriorated, and when the line width of the first sub-wiring 211 exceeds about 500 µm, an elongation may decrease and the stretchable characteristics may be deteriorated. Preferably, the line width of the first sub-wiring 211 may be about 100 µm to about 400 µm in consideration of the stretchable characteristics.

The first wiring 210 may have various shapes. For example, when viewed in a plane, each of the plurality of first sub-wirings 211 may have a linear shape extending in the first direction as shown in FIG. 12. Alternatively, when viewed in a plane, each of the plurality of first sub-wirings 211 may have a curved shape extending in the first direction as shown in FIG. 13. For example, each of the plurality of first sub-wirings 211 may be provided in a form in which a wavy pattern is repeated. In this case, the first sub-wiring 211 may have a curvature pattern of about 3 R to about 20 R (mm). Accordingly, when the mask 1000 is stretched or contracted in one direction, the first wiring 210 may have the stretchable characteristics and may not be cut. Preferably, the first sub-wiring 211 may have a curvature pattern of about 5 R to about 15 R (mm). Accordingly, the first wiring 210 may have more improved stretchable characteristics, thereby improving reliability.

In addition, the first wiring 210 may have an elongation of about 10% to about 50%. Alternatively, although not shown in the drawing, when viewed in a plane, each of the plurality of first sub-wirings 211 may have a shape in which a pattern in which a straight line and a curve extending in the first direction are mixed is repeated. For example, when viewed from a plane, the first sub-wiring 211 positioned in a region overlapping a relatively curved region of the user's face may be provided in a curved shape, and the first sub-wiring 211 positioned in a region overlapping a relatively planar region may be provided in a straight line. Accordingly, when the mask 1000A is attached to the user's face, it is possible to solve a problem that the first wiring 210 is damaged due to deformation of the mask 1000A. In addition, the first sub-wiring 211 may be provided in a form in which straight lines and curves are mixed to maintain electrical characteristics and at the same time reduce the ratio occupied by the first wire 210, thereby reducing overall manufacturing costs.

The piezoelectric element 300 may be disposed on the first substrate 110. In detail, the piezoelectric element 300 may be disposed on the first wiring 210 and electrically connected to the first wiring 210. The piezoelectric element 300 may include a ceramic material. As an example, the piezoelectric element 300 may include at least one of ZnO, AN, LiNbO$_4$, lead antimony stannate, lead magnesium tantalate, lead nickel tantalate, titanates, tungstates, zirconates, or lead including lead zirconate titanate [Pb(Zr$_x$Ti$_{1-x}$)O$_3$(PZT)], lead lanthanum zirconate titanate (PLZT), lead niobium Zirconate titanate (PNZT), BaTiO$_3$, SrTiO$_3$, lead magnesium niobate, lead nickel niobate, lead manganese niobate, lead zinc niobate, lead including lead titanate, barium, bismuth, or niobates of strontium.

The piezoelectric elements 300 may be disposed on the first wiring 210 in plural. In detail, a plurality of piezoelectric elements 300 may be disposed to be spaced apart from each other on the first sub-wiring 211. For example, the plurality of piezoelectric elements 300 may be disposed on one first sub-wiring 211, and the plurality of piezoelectric elements 300 may be spaced apart at equivalent intervals on the first sub-wiring 211. In addition, a piezoelectric element 300 disposed on one first sub-wiring 211 may or may not overlap a piezoelectric element 300 disposed on the first sub-wiring 211 closest to the one first sub-wiring 211 in the second direction. In addition, some of the piezoelectric elements 300 may be spaced apart at equivalent intervals, and the remaining piezoelectric elements 300 may not be disposed at equivalent intervals. For example, a space between the piezoelectric elements 300 may be disposed at equivalent intervals in a region overlapping a relatively flat region of the user's face surface. However, the space between the piezoelectric elements 300 may not be disposed at equivalent intervals in a region overlapping a relatively curved skin region. That is, the space between the piezoelectric elements 300 may be relatively narrow or large depending on the degree of curvature of the skin surface. Accordingly, the mask 1000A according to the embodiment may effectively provide vibration to the curved skin. In addition, the piezoelectric element 300 may be disposed on the entire region of the mask 1000A at predetermined intervals and generate evenly vibration in the entire region of the mask 1000A.

The piezoelectric element 300 may overlap the first sub-wiring 211. In detail, a lower surface of the piezoelectric element 300 may overlap the first sub-wiring 211 in the vertical direction.

The piezoelectric element 300 may generate vibration by an applied current. For example, the piezoelectric element 300 may generate ultrasonic vibration by the applied current. In detail, the piezoelectric element 300 may generate ultrasonic vibration of about 1 MHz or less. In more detail, the piezoelectric element 300 may generate ultrasonic vibration of about 10 KHz to about 1 MHz. In more detail, the piezoelectric element 300 may generate ultrasonic vibration of about 100 KHz to about 800 KHz. The ultrasonic vibration generated by the piezoelectric element 300 vibrates in a direction of one surface of the mask 1000A and is transmitted to the user's skin, thereby massaging the user's skin.

A thickness of the piezoelectric element 300 may be about 1500 μm or less. In detail, the thickness of the piezoelectric element 300 may be about 1200 μm or less. Preferably, the thickness of the piezoelectric element 300 may be about 1000 μm or less. It is preferable that the thickness of the piezoelectric element 300 satisfies the above-described range in consideration of the overall thickness and variable characteristics of the mask 1000A.

The piezoelectric element 300 may have various shapes. For example, the piezoelectric element 300 may have a polygonal column shape in which lower and upper surfaces are polygonal, and the lower and upper surfaces may have a circular column shape. In addition, one surface of the lower and upper surfaces of the piezoelectric element 300 may be a polygon and the other surface may have a pillar shape. As an example, an area of at least one of the lower surface and the upper surface of the piezoelectric element 300 may be about 100 mm2 or less.

As described above, the piezoelectric element 300 may have various pillar shapes, and intensity of ultrasonic vibration and an oscillation direction of vibration generated according to the pillar shape may be controlled. In addition, the intensity of vibration transmitted to the user's skin may be adjusted according to a size, arrangement interval, arrangement density, and the like of the piezoelectric element 300.

The piezoelectric element 300 may generate various waves. As an example, the piezoelectric element 300 may generate at least one wave of a transverse wave in which a traveling direction of wave and a vibration direction of medium are perpendicular, and a longitudinal wave in which the traveling direction of wave and the vibration direction of medium are the same. In addition, the piezoelectric element 300 may multiple-resonate. For example, the piezoelectric element 300 may include at least one via hole and may multiple-resonate by the formed via holes. In this case, an upper area of the via holes may be about 10% to about 45% of an area of the upper surface of the piezoelectric element 300 for multiple resonance. In addition, when the piezoelectric element 300 multiple-resonates by the via holes, the number of multiple resonance frequency regions may correspond to the number of the via holes. That is, the piezoelectric element 300 may emit wavelengths of various frequency ranges as the number of the via holes increases in a set number range of via holes.

The second substrate 120 may be disposed on the piezoelectric element 300. The second substrate 120 may be transparent and include a material in consideration of moisture barrier properties, thermal stability, and the like. In addition, the second substrate 120 may include a material that has flexibility and varies according to a shape of the user's curved skin. As an example, the second substrate 120 may include a resin material such as polyethylene terephthalate (PET), polyethylene naphthalate (PEN), and polyimide (PI). The second substrate 120 may be provided in a form of a film. The second substrate 120 may be provided with the same material as the first substrate 110 and may have the same shape.

The second substrate 120 may have a thickness of about 0.5 μm to about 5 μm. When the thickness of the second substrate 120 is less than about 0.5 μm, there may be a problem that a region of the second substrate 120 overlapping the components is struck by a weight of the components disposed on the second substrate 120, for example, the piezoelectric element 300. Accordingly, reliability of the second substrate 120 may be deteriorated, and a problem of alignment of the components disposed on the second substrate 120 may occur. In addition, when the thickness of the second substrate 120 exceeds about 5 μm, the overall thickness of the mask 1000 may be increased. Accordingly, there is a problem that the mask 1000 may not be efficiently varied according to the shape of the user's skin, and thus the mask 1000 does not effectively adhere to the user's skin. Preferably, the second substrate 120 may have a thickness of about 0.5 μm to about 3 μm. When the thickness of the second substrate 120 satisfies the above-described range, the second substrate 120 may be efficiently varied in a form corresponding to the user's skin and the overall thickness and weight of the mask 1000 may be reduced while maintaining reliability and alignment characteristics. The second substrate 120 may have the same thickness as the first substrate 110.

The second wiring 220 may be disposed on the second substrate 120. The second wiring 220 may be electrically connected to the piezoelectric element 300. The second wiring 220 may include a conductive material. For example, the second wiring 220 may include at least one metal of aluminum (Al), copper (Cu), silver (Ag), gold (Au), chromium (Cr), nickel (Ni), molybdenum (Mo), titanium (Ti), and alloys thereof. In addition, the second wiring 220 may include a non-metal such as carbon, and the like. The second wiring 220 may include the same material as the first wiring 210.

The second wiring 220 may be disposed on one surface of the second substrate 120 facing the piezoelectric element 300. That is, the second wiring 220 may be disposed on one surface opposite to the other surface of the second substrate 120 facing the user's skin. The second wiring 220 may be in direct contact with one surface of the second substrate 120 and may extend in a different direction from the first wiring 210. For example, the second wiring 220 may extend in the second direction different from the first direction in which the first wiring 210 extends. The second wiring 220 may be formed on one surface of the second substrate 120 by a process such as deposition or printing.

The second wiring 220 may include a plurality of second sub-wirings 221 disposed on the second substrate 120. The plurality of second sub-wirings 221 may extend in the second direction and may be spaced apart from each other in the first direction. The plurality of second sub-wirings 221 may be electrically connected to each other.

The second sub-wiring 221 may overlap the piezoelectric element 300. In detail, the second sub-wiring 221 may overlap the upper surface of the piezoelectric element 300 in the vertical direction.

The first wiring 210 and the second wiring 220 may be disposed to cross each other. In detail, when viewed in a plane as shown in FIG. 12, the first sub-wiring 211 and the second sub-wiring 221 may be disposed to cross each other in a mesh shape, and an open region OA in which the electrodes 210 and 220 are not disposed may be formed between the sub-wirings 211 and 221.

A thickness of the second sub-wiring 221 may be about 2 μm to about 50 μm. In detail, the thickness of the second sub-wiring 221 may be about 2 μm to about 40 μm. When the thickness of the second sub-wiring 221 is less than about 2 μm, electrical characteristics may be deteriorated, and it may be difficult to form uniformly. In addition, when the thickness of the second sub-wiring 221 exceeds about 50 μm, the overall thickness of the mask 1000A may increase, and a manufacturing time of the second wiring 220 may increase. In addition, the thickness of the second sub-wiring 221 is too thick, and thus stretchable characteristics may be deteriorated. Preferably, the thickness of the second sub-wiring 221 may be about 30 μm or less in consideration of stretchable characteristics in the horizontal direction, reliability, and process efficiency. The thickness of the second sub-wiring 221 is provided equal to the thickness of the first sub-wiring 211, so that process efficiency may be improved.

In addition, a line width of the second sub-wiring 221 may be greater than the thickness of the second sub-wiring 221. For example, the line width of the second sub-wiring 221 may be about 50 μm to about 500 μm. In detail, the line width of the second sub-wiring 221 may be about 100 μm to about 450 μm. When the line width of the second sub-wiring 221 is less than about 50 μm, reliability may be deteriorated, and when the line width of the second sub-wiring 221 exceeds about 500 μm, an elongation may decrease and the stretchable characteristics may be deteriorated. Preferably, the line width of the second sub-wiring 221 may be about 100 μm to about 400 μm in consideration of the stretchable characteristics. The line width of the second sub-wiring 221 is provided equal to the line width of the first sub-wiring 211, so that process efficiency may be improved.

The second wiring 220 may have various shapes. For example, when viewed in a plane, each of the plurality of second sub-wirings 221 may have a linear shape extending in the second direction as shown in FIG. 12. Alternatively, when viewed in a plane, each of the plurality of second sub-wirings 221 may have a curved shape extending in the second direction as shown in FIG. 13. For example, each of the plurality of second sub-wirings 221 may be provided in a form in which a wavy pattern is repeated. In this case, the second sub-wiring 221 may have a curvature pattern of about 3 R to about 20 R (mm). Accordingly, when the mask 1000A is stretched or contracted in one direction, the second wiring 220 may have the stretchable characteristics and may not be cut. Preferably, the second sub-wiring 221 may have a curvature pattern of about 5 R to about 15 R (mm). Accordingly, the second wiring 220 may have more improved stretchable characteristics, thereby improving reliability.

In addition, the second wiring 220 may have an elongation of about 10% to about 50%. Alternatively, although not shown in the drawing, when viewed in a plane, each of the plurality of second sub-wirings 221 may have a shape in which a pattern in which a straight line and a curve extending in the second direction are mixed is repeated. For example, when viewed in a plane, the second sub-wiring 221 positioned in a region overlapping a relatively curved region of the user's face may be provided in a curved shape, and the second sub-wiring 221 positioned in a region overlapping a relatively planar region may be provided in a straight line. Accordingly, when the mask 1000A is attached to the user's face, it is possible to solve a problem that the second wiring 220 is damaged due to deformation of the mask 1000A. In addition, the second sub-wiring 221 may be provided in a form in which straight lines and curves are mixed to maintain electrical characteristics and at the same time reduce the ratio occupied the second wiring 220, thereby reducing overall manufacturing costs.

It is preferable that the second wiring 220 has the same shape as the first wiring 210 in consideration of the stretchable characteristic of the mask 1000A. That is, it is preferable that the first wiring 210 and the second wiring 220 disposed in the same region have the same shape as each other.

In addition, although not shown in the drawings, the second wiring 220 may extend on the second substrate 120 in the same direction as the first wiring 210. That is, the second wiring 220 may extend in the same first direction as the first wiring 210.

The mask 1000 according to the embodiment may include the second base layer 520. The second base layer 520 may be disposed on the second substrate 120. The second base layer 520 may be disposed on the other surface opposite to the one surface of the second substrate 120. The second base layer 520 may be disposed in direct contact with the other surface of the second substrate 120.

The second base layer 520 is a portion that may be in contact with the skin while facing the user's skin, and may include a material harmless to the human body. In addition, the second base layer 520 may include a soft and elastic material. For example, the second base layer 520 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second base layer 520 may include a silicone elastomer among them that is relatively light, can minimize irritation upon contact with the user's skin, and has a predetermined elasticity.

The second base layer 520 may be disposed to cover the entire region of the other surface of the second substrate 120. That is, when viewed in a plane, a plan area of the second base layer 520 may correspond to an area of the other surface of the second substrate 120. In addition, the plan area of the second base layer 520 may be greater than the area of the other surface of the second substrate 120. Accordingly, the second base layer 520 may be disposed surrounding a side surface of the second substrate 120. The second base layer 520 may prevent the other surface of the second substrate 120 from being exposed to the outside.

In addition, the second base layer 520 may pass through the wavelengths emitted from the piezoelectric element 300 in the direction of one surface of the mask 1000 to transmit the wavelengths to the user's skin. That is, the second base layer 520 may be a transmission layer. To this end, a thickness of the second base layer 520 may vary depending on an impedance of the second base layer 520 and a driving frequency of the piezoelectric element 300. As an example, when the driving frequency of the piezoelectric element 300 is about 1 MHz or less, the thickness of the second base layer 520 may be about 50 μm to about 1 mm. When the thickness of the second base layer 520 is less than about 50 μm, the thickness of the second base layer 520 is relatively small, so that the second substrate 120 may not be effectively protected. In addition, when the thickness of the second base layer 520 exceeds about 1 mm, the thickness of the entire mask 1000A may be increased. It is preferable that the thickness of the second base layer 520 satisfies the above-described range in order to effectively pass through the wavelengths emitted from the piezoelectric element 300. Preferably, the thickness of the second base layer 520 may have a thickness range of 100 μm to about 700 μm in consideration of reliability, transmission characteristics, and the thickness and weight of the mask 1000A to be manufactured.

The mask 1000A according to the embodiment may include a first base layer 510. The first base layer 510 may be disposed under the first substrate 110. The first base layer 510 may be disposed on the other surface opposite to one surface of the first substrate 110. The first base layer 510 may be disposed in direct contact with the other surface of the first substrate 110.

The first base layer 510 may include a material harmless to the human body. In addition, the first base layer 510 may include a soft and elastic material. For example, the first base layer 510 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the first base layer 510 may include a silicone elastomer among them that is relatively light, can minimize irritation upon contact with the user's skin, and has a predetermined elasticity. The first base layer 510 may be provided with the same material as the second base layer 520.

The first base layer 510 may be disposed to cover the entire region of the other surface of the first substrate 110. That is, when viewed in a plane, a plan area of the first base layer 510 may correspond to an area of the other surface of the first substrate 110. In addition, the plan area of the first base layer 510 may be greater than the area of the other surface of the first substrate 110. Accordingly, the first base layer 510 may be disposed surrounding a side surface of the first substrate 110. The first base layer 510 may prevent the other surface of the first substrate 110 from being exposed to the outside.

In addition, the first base layer 510 may reflect the wavelengths emitted from the piezoelectric element 300 in a direction of one surface of the mask 1000. That is, the first base layer 510 may be a reflective layer. To this end, a thickness of the first base layer 510 may be equal to or smaller than a thickness of the second base layer 520. In detail, the thickness of the first base layer 510 may be equal to or smaller than the thickness of the second base layer 520 in order to reflect the wavelengths emitted from the piezoelectric element 300 toward the first substrate 110 to the first base layer 510.

The thickness of the first base layer 510 may be about 50 μm to about 1 mm. When the thickness of the first base layer 510 is less than about 50 μm, the thickness of the first base layer 510 is relatively small, so that the first substrate 110 may not be effectively protected. In addition, when the thickness of the first base layer 510 exceeds about 1 mm, the thickness of the entire mask 1000A may be increased, and most of the wavelengths emitted from the piezoelectric element 300 in a direction of the first substrate 110 pass through the first base layer 510 and are reflected by the first base layer 510, so that the amount of reflection in the direction of one surface of the mask 1000A may be small. In addition, a required thickness of the second base layer 520 to be described later may be increased for reflection in the direction of one surface of the mask 1000, and a region of the wavelengths generated from the piezoelectric element 300 is high for reflection, and thus it may not be suitable for use in the mask 1000A. Therefore, it is preferable that the thickness of the first base layer 510 satisfies the above-described range in order to prevent the above problems. More preferably, the thickness of the first base layer 510 may be about 100 μm to about 700 μm. That is, it is preferable that the first base layer 510 has a thickness range of about 100 μm to about 700 μm in consideration of reliability, reflective properties, and the thickness and weight of the mask 1000A to be manufactured.

In addition, the first base layer 510 may have pores or the like formed therein in order to effectively reflect the wavelengths generated from the piezoelectric element 300. In addition, one surface of the first base layer 510 facing the piezoelectric element 300 may include at least one groove concave from the one surface toward the other surface opposite to the one surface. The groove may be disposed at a position overlapping the piezoelectric element 300 in the vertical direction and may be filled with air or the like to reflect the wavelengths of the piezoelectric element 300 upward, for example, toward the second substrate.

Accordingly, the wavelengths emitted from the piezoelectric element 300 may be transmitted to the user through the second substrate 120 and the second base layer 520, and the wavelengths emitted toward the first substrate 110 may be reflected to the first base layer 510 to be effectively transmitted to the user's skin.

The mask 1000A according to the embodiment may include at least one sensing unit 700. The sensing unit 700 may be disposed between the first substrate 110 and the second substrate 120. The sensing unit 700 may overlap the open region OA in the vertical direction. That is, the sensing unit 700 may be disposed in a region that does not overlap the first wiring 210 and the second wiring 220 based on the vertical direction. In addition, the sensing unit 700 may be disposed in a region that does not overlap the piezoelectric element 300 based on the vertical direction.

The sensing unit 700 may include a conductive material. For example, the sensing unit 700 may include a metal material. In detail, the sensing unit 700 may include at least one metal of aluminum (Al), copper (Cu), silver (Ag), gold (Au), chromium (Cr), nickel (Ni), molybdenum (Mo), titanium (Ti), and alloys thereof. In addition, the sensing unit 700 may include a metal oxide. In detail, the sensing unit 700 may include a metal oxide such as indium tin oxide, indium zinc oxide, copper oxide, tin oxide, zinc oxide, and titanium oxide, or the like. In addition, the sensing unit 700 may include a nanowire, a photosensitive nanowire film, a carbon nanotube (CNT), graphene, a conductive polymer, or a mixture thereof. The sensing unit 700 may have a flexible characteristic by including the above-described material. Preferably, the sensing unit 700 may include a metal material. As an example, the sensing unit 700 may be provided with the same material as the first wiring 210 and/or the second wiring 220 so as to be formed together when forming the first wiring 210 and/or the second wiring 220.

The sensing unit 700 may include a first sensing electrode 710 and a second sensing electrode 720 spaced apart from each other.

The first sensing electrode 710 may be disposed on the first substrate 110. The first sensing electrode 710 may be disposed on one surface of the first substrate 110 facing the user's skin. The first sensing electrode 710 may be disposed in direct contact with one surface of the first substrate 110. The first sensing electrode 710 may be disposed on the same plane as the first wire 210 and may extend in a different direction from the first wire 210. For example, the first sub-wiring 211 may extend in the first direction, and the first sensing electrode 710 may extend in the second direction different from the first direction.

The first sensing electrode 710 may be connected to the first wiring 210. In detail, the first sensing electrode 710 may be electrically connected to the first wire 210 by a wiring 215 extending from the first sub-wiring 211. In detail, the wiring 215 may extend from the first wiring 210 to the open region OA to be physically and electrically connected to the first sensing electrode 710.

The wiring 215 may be formed at the same time as the first wiring 210 in a process of forming the first wiring 210. Accordingly, the wiring 215 may include the same material as the first wiring 210. In addition, the wiring 215 may have the same line width and thickness as the first sub-wiring 211.

Alternatively, the wiring 215 may be formed at the same time as the first sensing electrode 710 in a process of forming the first sensing electrode 710 and may include the same material as the first sensing electrode 710.

Still alternatively, the wiring 215 may be formed together in a process of simultaneously forming the first wiring 210 and the first sensing electrode 710. In this case, the wiring 215, the first wiring 210, and the first sensing electrode 710 may include the same material. In addition, the first wiring 210, the first sensing electrode 710, and the wiring 215 may have the same thickness.

The second sensing electrode 720 may be disposed on the second substrate 120. The second sensing electrode 720 may be disposed on one surface of the second substrate 120 facing the piezoelectric element 300. The second sensing electrode 720 may be disposed in direct contact with one surface of the second substrate 120. The second sensing electrode 720 may be disposed on the same plane as the second wire 220 and may extend in a different direction from the second wire 220. For example, the second sub-wiring 221 may extend in the second direction, and the second sensing electrode 720 may extend in the first direction different from the second direction.

The second sensing electrode 720 may be connected to the second wiring 220. In detail, the second sensing electrode 720 may be electrically connected to the second wire 220 by a wire 225 extending from the second sub-wiring 221. In detail, the second wire 225 may extend from the second wire 220 to the open region OA to be physically and electrically connected to the second sensing electrode 720.

The wiring 225 may be formed at the same time as the second wiring 220 in a process of forming the second wiring 220. Accordingly, the wiring 225 may include the same material as the second wiring 220. In addition, the wiring 225 may have the same line width and thickness as the second sub-wiring 221.

Alternatively, the wiring 225 may be formed at the same time as the second sensing electrode 720 in a process of forming the second sensing electrode 720 and may include the same material as the second sensing electrode 720.

Still alternatively, the wiring 225 may be formed together in a process of simultaneously forming the second wiring 220 and the second sensing electrode 720. In this case, the second wiring 225, the second wiring 220, and the second sensing electrode 720 may include the same material. In addition, the second wiring 220, the second sensing electrode 720, and the wiring 225 may have the same thickness.

The first sensing electrode 710 and the second sensing electrode 720 may be disposed in the same open region OA. In addition, the first sensing electrode 710 and the second sensing electrode 720 may not vertically overlap within the open region OA. That is, as shown in FIG. 5, the first sensing electrode 710 and the second sensing electrode 720 may be horizontally spaced apart in the open region OA. A horizontal distance dl between the first sensing electrode 710 and the second sensing electrode 720 may be several hundred micrometers or less.

The first sensing electrode 710 and the second sensing electrode 720 may have various shapes. For example, a planar shape of the first sensing electrode 710 and the second sensing electrode 720 may have at least one planar shape of shapes including a circle, a polygon, a straight line, and a curve. The first sensing electrode 710 and the second sensing electrode 720 may have the same planar shape. In addition, the first sensing electrode 710 and the second sensing electrode 720 may have the same plane area. Accordingly, a change in a capacitance value between the first sensing electrode 710 and the second sensing electrode 720 may be effectively detected.

The mask 1000A according to the embodiment may include a control unit (not shown). The control unit may be connected to the first wiring 210, the second wiring 220, and the sensing unit 700. The control unit may operate the piezoelectric element 300 by applying a current to the first wiring 210 and the second wiring 220 by an input signal. In addition, the control unit may detect a change in the capacitance value through the sensing unit 700. In detail, the control unit may detect a change in the capacitance value between the first sensing electrode 710 and the second sensing electrode 720.

The mask 1000A may detect a change in the capacitance value in real time in a process of generating vibration by applying a current to the piezoelectric element 300.

For example, the control unit may generate vibration by applying a signal defined as a first mode and may detect a change in the capacitance value by applying a signal defined as another second mode.

In detail, when the mask 1000A operates in the first mode, the control unit may apply current to the first wiring 210 and the second wiring 220. Accordingly, vibration may be generated in the piezoelectric element 300. In addition, when the mask 1000A operates in the second mode, the control unit may apply current to the first sensing electrode 710 and the second sensing electrode 720. Accordingly, the sensing unit 700 may detect a change in the capacitance value The control unit may control an operation order of the first and second modes. For example, the control unit may apply a signal to the wirings 210 and 220 and the sensing unit 700 in the order of "first mode-second mode", and the mask 1000A may operate in the order of "vibration generation-capacitance change detection".

In addition, the control unit may control an operation time of the first and second modes. For example, the first mode may operate for a first time to generate vibration. Further, the second mode may operate for a second time shorter than the first time to detect a change in the capacitance value. Here, the second time may be a very short time that may not be detected by the human and a time sufficient to detect a change in the capacitance value. That is, the mask 1000A may operate in the first mode for a set time and detect a change in the capacitance value for a short time that is difficult for the user to experience. Subsequently, the mask 1000A may operate in the first mode again. That is, when the mask 1000A is operated, the user may recognize that vibration is continuously provided to the skin, and at the same time, the mask 1000A may periodically detect whether the mask 1000A is in contact with the skin.

The mask 1000A according to the embodiment may include the first protective layer 551. The first protective layer 551 may be disposed between the first substrate 110 and the second substrate 120. The first protective layer 551 may be disposed in direct contact with one surface of the first substrate 110 and one surface of the second substrate 120.

The first protective layer 551 may include a material having softness and elasticity. For example, the first protective layer 551 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The first protective layer 551 may be preferable to include a silicone elastomer among them that is relatively light, can minimize irritation upon contact with the user's skin, and has a predetermined elasticity.

The first protective layer 551 may be disposed between the first substrate 110 and the second substrate 120 to protect the piezoelectric element 300 and the sensing unit 700. In detail, the first protective layer 551 may be disposed between the substrates 110 and 120 to surround the piezoelectric element 300 and the sensing unit 700 to protect the components. In addition, the first protective layer 551 may be connected to the first base layer 510 and the second base layer 520. That is, the first base layer 510, the second base layer 520, and the first protective layer 551 may be integrally formed to be physically connected and support a component disposed therein.

In more detail, the piezoelectric element 300 may include a first electrode 310 disposed on a lower surface thereof. The first electrode 310 may be disposed in an area of about 80% or more of the entire area of the lower surface of the piezoelectric element 300 in consideration of electrical characteristics. In detail, the first electrode 310 may be disposed in an area of about 90% of the entire area of the lower surface of the piezoelectric element 300. In addition, the first electrode 310 may be disposed on the entire region of the lower surface of the piezoelectric element 300. However, there is a problem that it is difficult to form the first electrode 310 while covering the entire region in the electrode formation process, and thus it may be preferable that a ratio occupied by the first electrode 310 satisfies the above-described range.

The first electrode 310 may include a conductive material. As an example, the first electrode 310 may include a metal material. In detail, the first electrode 310 may include at least one metal of aluminum (Al), copper (Cu), silver (Ag), gold (Au), chromium (Cr), nickel (Ni), molybdenum (Mo), titanium (Ti), and alloys thereof.

The first electrode 310 may be disposed facing the first wiring 210 and may be electrically connected to the first wiring 210. In detail, the first bonding layer 251 may be disposed between the first electrode 310 and the first wiring 210, and the first electrode 310 and the first wiring 210 may be physically and electrically connected by the first bonding layer 251. In this case, the overlapping ratio between the first bonding layer 251 and the first wiring 210 may be about 20% or more in consideration of physical and electrical connection characteristics.

The first bonding layer 251 may include at least one metal of aluminum (Al), copper (Cu), silver (Ag), gold (Au), chromium (Cr), nickel (Ni), molybdenum (Mo), titanium (Ti), and alloys thereof. The first bonding layer 251 may be disposed between the first electrode 310 and the first wiring 210 to serve as a conductive adhesive. As an example, the first bonding layer 251 may be applied in the form of the paste on the first wiring 210, and the piezoelectric element 300 including the first electrode 310 may be disposed on the first bonding layer 251. Accordingly, the piezoelectric element 300 may be physically and electrically connected to the first wiring 210.

In addition, the piezoelectric element 300 may include the second electrode 320 disposed on an upper surface thereof. The second electrode 320 may be disposed in an area of about 80% or more of the entire area of the upper surface of the piezoelectric element 300 in consideration of electrical characteristics. In detail, the second electrode 320 may be disposed in an area of about 90% of the entire area of the upper surface of the piezoelectric element 300. In addition, the second electrode 320 may be disposed on the entire region of the lower surface of the piezoelectric element 300. However, there is a problem in that it is difficult to form the second electrode 320 while covering the entire region in the electrode formation process, and thus it may be preferable that the ratio occupied by the second electrode 320 satisfies the above-described range.

The second electrode 320 may include a conductive material. As an example, the second electrode 320 may include a metal material. In detail, the second electrode 320 may include at least one metal of aluminum (Al), copper (Cu), silver (Ag), gold (Au), chromium (Cr), nickel (Ni), molybdenum (Mo), titanium (Ti), and alloys thereof.

The second electrode 320 may be disposed facing the second wiring 220 and may be electrically connected to the second wiring 220. In detail, the second bonding layer 252 may be disposed between the second electrode 320 and the second wiring 220, and the second electrode 320 and the second wiring 220 may be physically and electrically connected by the second bonding layer 252. In this case, the overlapping ratio between the second bonding layer 252 and the second wiring 220 may be about 20% or more in consideration of physical and electrical connection characteristics.

The second bonding layer 252 may include at least one metal of aluminum (Al), copper (Cu), silver (Ag), gold (Au), chromium (Cr), nickel (Ni), molybdenum (Mo), titanium (Ti), and alloys thereof. The second bonding layer 252 may be disposed between the second electrode 320 and the second wiring 220 to serve as a conductive adhesive. As an example, the second bonding layer 252 may be applied in the form of the paste on the second wiring 220, and the piezoelectric element 300 including the second electrode pad 310 may be disposed on the second bonding layer 252. Accordingly, the piezoelectric element 300 may be physically and electrically connected to the second wiring 220, and the first substrate 110 and the second substrate 120 may be spaced apart from each other at a predetermined interval.

The first bonding layer 251 may be provided with the same thickness as the second bonding layer 252 to improve the variability of the mask 1000A. In addition, the thickness of the first bonding layer 251 may be different from the thickness of the second bonding layer 252. In detail, the thickness of the first bonding layer 251 may be greater than the thickness of the second bonding layer 252. Accordingly, the wavelengths emitted from the piezoelectric element 300 toward the first substrate 110 may be reflected by the first bonding layer 251 to move toward the second substrate 120.

In addition, the mask 1000A may further include a third bonding layer (not shown). The third bonding layer may be disposed on the other surface of the first substrate 110. That is, the third bonding layer may be disposed between the other surface of the first substrate 110 and the first base layer 510. Accordingly, the wavelengths emitted from the piezoelectric element 300 toward the first substrate 110 may be reflected by the third bonding layer to move toward the second substrate 120. Accordingly, it is possible to minimize the loss of wavelengths emitted from the piezoelectric element 300

Thereafter, as described above, the first protective layer 551 may be filled in a space between the first substrate 110 and the second substrate 120. Accordingly, the first protective layer 551 may be disposed surrounding the piezoelectric element 300, the light-emitting element 400, the first wiring 210, the second wiring 220, and the sensing unit 700 and may prevent the components from being directly exposed to the external environment.

FIGS. 16 and 17 are views illustrating a change in a capacitance value of a sensing unit depending on whether the mask and the skin are in contact with each other according to the second embodiment. In addition, FIG. 18 is a view illustrating that the mask according to the second embodiment includes a plurality of sensing units.

Referring to FIGS. 16 to 18, the mask 1000A according to the embodiment may be in contact with the user's skin 50. For example, the mask 1000A may be in direct contact with the user's skin 50, and as shown in the drawing, a cosmetic or a drug 60 may be disposed between the mask 1000A and the skin 50 to be in direct or indirect contact with each other.

Referring to FIG. 16, the mask 1000A according to the embodiment may directly or indirectly contact the user's skin 50. In this case, the capacitance value of the sensing unit 700 may change. In detail, the capacitance value of the sensing unit 700 may be changed by a current flowing through the user's skin. For example, when the mask 1000A and the user's skin 50 contact each other, a capacitance may be formed to be divided between the first sensing electrode 710 and the skin 50, the second sensing electrode 720 and the skin 50, and the first sensing electrode 710 and the second sensing electrode 720. Accordingly, the control unit may recognize a change in the capacitance value of the sensing unit 700 to recognize a state in which the mask 1000A is in contact with the user's skin 50.

In addition, referring to FIG. 17, the mask 1000A according to the embodiment may be spaced apart from the user's skin 50. In this case, the capacitance value of the sensing unit 700 may not change. Accordingly, the control unit may recognize a state in which the mask 1000A and the user's skin 50 are separated from each other.

Referring to FIG. 18, the mask 1000A may include a plurality of sensing units 700. In detail, the sensing unit 700 may be provided at a position overlapping a relatively curved region of the user's face. As an example, the sensing unit 700 may be disposed at a position corresponding to a relatively curved region such as both cheeks, forehead, and chin. That is, the sensing unit 700 may be disposed on a region where the mask 1000A is difficult to adhere due to the curved skin surface to detect whether the mask 1000A and the skin 50 are closely adhered to each other.

FIG. 19 is a view illustrating an example in which an indicator is disposed on the mask according to the embodiment.

Referring to FIG. 19, the mask 1000 according to the embodiment may include an indicator 810. The indicator 810 may include at least one of members such as an LED, a display, a buzzer, and the like that may transmit visual or auditory information to a user.

The indicator 810 may be disposed outside the mask 1000 to display an operation state of the mask 1000. As an example, the indicator 810 may provide information about the start of the operation of the mask 1000, information notifying that the operation is in progress, and information about the completion of the operation through the auditory information generated from the buzzer. In addition, the indicator 810 may display the operation state according to the light emission color of the LED. In addition, the indicator may display information on an operating frequency domain through the display.

In addition, the indicator 810 may provide information on whether the mask 1000 and the skin 50 are closely adhered to each other. In detail, the mask 1000 may include the sensing unit 700 as in the second embodiment described above. Accordingly, the mask 1000 may detect a change in the capacitance value between the first sensing electrode 710 and the second sensing electrode 720. As an example, when the sensing unit 700 disposed on the region corresponding to the forehead cannot detect a change in the capacitance value, the indicator 810 may inform the user through the visual or auditory information that the forehead portion of the mask 1000 is not closely adhered. Accordingly, the indicator 810 may provide information so that the mask 1000 and the user's skin are in effective contact with each other.

FIGS. 20 and 21 are views illustrating an example in which a protrusion is disposed on the mask according to an embodiment.

Referring to FIGS. 20 and 21, the mask 1000A may include a protrusion 820 disposed on an outer surface. In detail, the protrusion 820 may be disposed on one surface of the second base layer 520 facing the user's skin.

The protrusion 820 may include a material harmless to the human body and may be disposed to protrude from one surface of the second base layer 520 toward the user's skin. The protrusions 820 may be disposed in a form of a plurality of points spaced apart from each other on one surface of the second base layer 520. In addition, the protrusions 820 may be disposed in a form of a plurality of straight lines or curves spaced apart from each other on one surface of the second base layer 520. In addition, the protrusion 820 may be disposed in a single spiral shape on one surface of the second base layer 520.

In addition, the protrusion 820 may be applied to the mask 1000 according to the first embodiment described above. For example, although not shown in the drawing, the protrusion 820 may be disposed on one surface of the second base layer 520 in the mask 1000 of FIG. 5. In this case, the protrusion 820 may be spaced apart from the electrode layer 600. The protrusion 820 may be disposed in a region between the electrode layers 600.

When the user wears the masks 1000A and 1000, the protrusion 820 may form a predetermined space between the masks 1000A and 1000 and the user's skin. Accordingly, it is possible to prevent cosmetics or drugs between the masks 1000A and 1000 and the skin from being pushed out to an edge region of the masks 1000A and 1000 by the pressure generated when the masks 1000A and 1000 are worn and/or the vibration generated from the piezoelectric element 300. That is, the protrusion 820 may serve as a partition wall preventing cosmetics or drugs from getting out of the masks 1000A and 1000. Therefore, the user may effectively inject cosmetics or drugs into the skin using the masks 1000A and 1000.

FIG. 22 is a view illustrating a user wearing a mask according to the embodiment, and FIG. 23 is a view illustrating a skin care device to which the mask according to the embodiment is applied.

Referring to FIG. 22, the user may wear the mask 1000 according to the first embodiment or the mask 1000A according to the second embodiment. The masks 1000 and 1000A may include the above-described opening 1010, and a user may secure a view through the opening 1010. In addition, the masks 1000 and 1000A may include the above-described cutout portion 1020, and the masks 1000 and 1000A may be effectively close-adhered to the curved skin by the cutout portion 1020. In this case, one surface of the second base layer 520 may be in direct contact with the user's skin. In addition, drugs or cosmetics may be disposed between the second bath layer 520 and the user's skin, so that the base layer 520 may be in direct or indirect contact with the user's skin.

The masks 1000 and 1000A may be operated by receiving power through an external power connected to the masks 1000 and 1000A. In addition, the masks 1000 and 1000A may be operated by receiving power through a power supply unit (not shown) disposed outside the mask 1000, for example, on a lower surface of the first base layer 510.

In addition, referring to FIG. 23, the masks 1000 and 1000A may be applied to a skin care device 1 to operate. In detail, referring to FIG. 23, the skin care device 1 may include a main body 10 in which one side thereof is open and including an accommodation space 11 therein.

The main body 10 may include a material that may be light and prevent damage from external impact or contact. As an example, the main body 10 may include a plastic or ceramic material, may have improved reliability from an external environment, and may protect the masks 1000 and 1000A disposed inside the accommodation space 11. In addition, the main body 10 may include a viewing part 13 formed at a position corresponding to the user's eyes. The viewing part 13 is formed in a region corresponding to the opening 1010 of the masks 1000 and 1000A, and the user may secure an external view through the viewing part 13.

The masks 1000 and 1000A may be disposed in the accommodation space 11 of the main body 10. The masks 1000 and 1000A may be disposed between the main body 10 and the user's skin. In detail, the first base layer 510 of the masks 1000 and 1000A may be disposed to face the accommodation space 11 of the main body 10, and the second base layer 520 of the masks 1000 and 1000A may be disposed to face the user's skin.

The masks 1000 and 1000A may be coupled to the main body 10. For example, the masks 1000 and 1000A may be fixed to a set position in the accommodation space 11 by a fastening member (not shown) and may have a structure that is detachable from the main body 10.

The masks 1000 and 1000A may be supplied with power through the power supply unit (not shown) disposed outside the mask 1000, for example, on the lower surface of the first base layer 510. Alternatively, the masks 1000 and 1000A may be connected to the main body 10 to be supplied with power through the power supply unit (not shown) disposed on the main body 10.

The masks 1000 and 1000A may include a deformable member (not shown) disposed on the lower surface of the first base layer 510. The deformable member may be in direct contact with the first base layer 510 and may be disposed facing the accommodation space 11 of the main body 10. That is, the deformable member may be disposed between the main body 10 and the first base layer 510 of the masks 1000 and 1000A.

The deformable member may include a material of which shape is changed by external pressure. For example, the deformable member may include a material such as an air gap or a sponge, but the embodiment is not limited thereto, and may include various materials of which shape is changed by external pressure. Accordingly, when the user puts on the skin care device 1, the deformable member may be deformed into a shape corresponding to the shape of the user's face. Therefore, the ultrasonic mask 1000 and the user's skin may be effectively close-adhered to each other. In addition, when a plurality of users put on the skin care device 1, the deformable member is deformed to correspond to each face shape, so that the user's skin and the mask 1000 may be effectively close-adhered to each other.

The characteristics, structures, effects, and the like described in the above-described embodiments are included in at least one embodiment of the present invention, but are not limited to only one embodiment. Furthermore, the characteristic, structure, and effect illustrated in each embodiment may be combined or modified for other embodiments by a person skilled in the art. Thus, it should be construed that the contents related to such combination and modification are included in the scope of the present invention.

In addition, the above description has been focused on the embodiments, but it is merely illustrative and does not limit the present invention. Those skilled in the art to which the embodiments pertain may appreciate that various modifications and applications not illustrated above are possible without departing from the essential features of the embodiment. For example, each component particularly represented in the embodiments may be modified and realized. In addition, it should be construed that differences related to such a modification and an application are included in the scope of the present invention defined in the appended claims.

The invention claimed is:

1. A mask comprising: a first substrate; a first wiring disposed on the first substrate; a plurality of piezoelectric elements disposed on the first wiring; a second wiring disposed on the piezoelectric element; a second substrate disposed on the second wiring; a third wiring disposed on the first substrate and electrically insulated from the first wiring; and a plurality of light-emitting elements disposed between the first and second substrates and disposed on the third wiring, wherein the plurality of light-emitting elements are disposed in a region between the plurality of piezoelectric elements, wherein the light-emitting element includes a visible light-emitting element and an infrared light-emitting element disposed alternately with each other, and wherein the plurality of piezoelectric elements are disposed at different intervals according to the curved shape of a facial skin.

2. The mask of claim 1, further comprising:
a first base layer disposed under the first substrate and a second base layer disposed on the second substrate.

3. The mask of claim 2, comprising:
an electrode layer disposed on the second base layer,
wherein the electrode layer overlaps at least one of the piezoelectric element and the light-emitting element based on a vertical direction, and
the electrode layer has a line width of 550 μm or less and a thickness of 350 μm or less.

4. The mask of claim 3, wherein the first base layer includes the same material as the second base layer and has a thickness that is equal to or smaller than that of the second base layer.

5. The mask of claim 4, wherein a plurality of protrusions are disposed on one surface of the second base layer.

6. The mask of claim 5, wherein the second substrate includes a plurality of through-holes corresponding to each of the plurality of light-emitting elements.

7. The mask of claim 5, comprising:
a first protective layer disposed between the first and second substrates,
wherein the first protective layer is disposed surrounding the piezoelectric element and the light-emitting element.

8. The mask of claim 1, comprising:
a first region and a second region,
wherein the visible light-emitting element is disposed at a ratio greater than that of the infrared light-emitting element in the first region,
the infrared light-emitting element is disposed at a ratio greater than that of the visible light-emitting element in the second region.

9. The mask of claim 1, wherein elongation of the first wiring and the second wiring is 10% to 50%.

10. The mask of claim 1, further comprising:
an indicator disposed on the second substrate.

11. The mask of claim 1, comprising:
a sensing unit disposed between the first substrate and the second substrate,
wherein the sensing unit includes:
a first sensing electrode connected to the first wiring; and
a second sensing electrode connected to the second wiring, and
the first and second sensing electrodes do not overlap each other based on a vertical direction.

12. The mask of claim 11, wherein the sensing unit does not overlap the piezoelectric element based on the vertical direction.

13. A skin care device comprising:
a main body in which one side thereof is an open region and an accommodation space is formed inside the open region; and
the mask of claim 1 which is disposed in the open region and connected to the main body.

14. The skin care device of claim 13, comprising:
a sensing unit disposed between the first substrate and the second substrate,
wherein the sensing unit includes:
a first sensing electrode connected to the first wiring; and
a second sensing electrode connected to the second wiring, and
the first and second sensing electrodes do not overlap each other based on a vertical direction.

* * * * *